(12) United States Patent
Hwang et al.

(10) Patent No.: US 8,993,839 B2
(45) Date of Patent: Mar. 31, 2015

(54) PLANT-BASED PRODUCTION OF HETEROLOGOUS PROTEINS

(75) Inventors: Minsook Hwang, Davis, CA (US); Benjamin E. Lindenmuth, Davis, CA (US); Karen A. McDonald, Davis, CA (US); Abhaya M. Dandekar, Davis, CA (US); Bryce W. Falk, Davis, CA (US); Sang-Kyu Jung, Davis, CA (US); Nathaniel J. Kingsbury, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 820 days.

(21) Appl. No.: 13/186,423

(22) Filed: Jul. 19, 2011

(65) Prior Publication Data

US 2012/0045818 A1 Feb. 23, 2012

Related U.S. Application Data

(60) Provisional application No. 61/399,905, filed on Jul. 19, 2010, provisional application No. 61/399,904, filed on Jul. 19, 2010.

(51) Int. Cl.
| | | |
|---|---|---|
| *C12N 15/83* | (2006.01) | |
| *C12N 9/42* | (2006.01) | |
| *C12N 15/87* | (2006.01) | |
| *C12N 5/04* | (2006.01) | |
| *C12N 15/09* | (2006.01) | |
| *C12N 15/40* | (2006.01) | |
| *C12N 15/82* | (2006.01) | |
| *C12P 21/02* | (2006.01) | |

(52) U.S. Cl.
CPC ........ *C12N 15/8257* (2013.01); *C12N 15/8203* (2013.01); *C12N 15/8216* (2013.01); *C12P 21/02* (2013.01); *C12Y 302/01006* (2013.01); *C12N 9/244* (2013.01)
USPC .......... 800/280; 800/288; 800/294; 435/69.1; 435/468; 435/469; 435/475; 435/209; 435/320.1; 435/419; 536/23.2; 536/23.7; 536/23.72

(58) Field of Classification Search
None
See application file for complete search history.

(56) References Cited

U.S. PATENT DOCUMENTS

| | | | |
|---|---|---|---|
| 5,902,581 A | 5/1999 | Clarkson et al. | |
| 7,034,128 B2 | 4/2006 | Turpen et al. | |
| 2007/0300330 A1* | 12/2007 | Marillonnet et al. | 800/294 |

FOREIGN PATENT DOCUMENTS

| | | |
|---|---|---|
| WO | 00/46350 A1 | 8/2000 |
| WO | 2004/011614 A2 | 2/2004 |
| WO | 2007/005882 A2 | 1/2007 |
| WO | 2008/036424 A2 | 3/2008 |

OTHER PUBLICATIONS

Pio-Ribeiro et al (Phytopathology, 68, pp. 1260-1265, 1978).*
Martin et al (J. Gen. Virol, 90(11), pp. 2815-2820, 2009; published online ahead of print Jul. 8, 2009).*
Sudarshana et al (Plant Biotechnology Journal, 4, pp. 551-559, 2006).*
Pierrugues et al (Journal of General Virology, 88, pp. 2852-2861, 2007).*
Matsuo et al (Planta, 225, pp. 277-286, 2007).*
Ransom et al (Applied Biochemistry and Biotechnology, 136-140, pp. 207-219, 2007).*
Kim et al (J. Gen. Virol., 85(1), pp. 221-230, 2004).*
Bonnett et al (Virology, 332(1), pp. 359-368, 2005).*
International Search Report and Written Opinion received for PCT Patent Application No. PCT/US2011/044578, mailed on Mar. 27, 2012, 11 pages.
International Preliminary Report on Patentability received for PCT Patent Application No. PCT/US2011/044578 mailed on Jan. 31, 2013, 7 pages.
Extended European Search Report (includes Supplementary European Search Report and Search Opinion) received for European Patent Application No. 11810305.0, mailed on Oct. 24, 2013, 11 pages.
Office Action received for New Zealand Patent Application No. 605892, mailed on Jul. 18, 2013, 2 pages.
Chen et al., "Transferred DNA (T-DNA)-Associated Proteins of Agrobacterium Tumefaciens are Exported Independently of virB", PNAS, vol. 97, No. 13, Jun. 20, 2000, pp. 7545-7550.
Dujovny et al., "A Temperature-Controlled Amplicon System Derived from Plum Pox Potyvirus", Plant Biotechnology Journal, vol. 7, 2009, pp. 49-58.
Fujiki et al., "Development of a New Cucumber Mosaic Virus-Based Plant Expression Vector with Truncated 3a Movement Protein", Virology, vol. 381, 2008, pp. 136-142.
Fullner et al., "Temperature Affects the T-DNA Transfer Machinery of Agrobacterium Tumefaciens", Journal of Bacteriology, vol. 178, No. 6, Mar. 1996, pp. 1498-1504.
Giritch et al., "Rapid High-Yield Expression of Full-Size IgG Antibodies in Plants Coinfected with Noncompeting Viral Vectors", PNAS, vol. 103, No. 40, Oct. 3, 2006, pp. 14701-14706.

(Continued)

*Primary Examiner* — David T Fox
*Assistant Examiner* — Stephen Uyeno
(74) *Attorney, Agent, or Firm* — Morrison & Foerster LLP

(57) ABSTRACT

Described herein are viral amplicon-based protein expression systems and methods useful for producing heterologous proteins, such as enzymes, by agroinfiltration. The methods involve producing an *Agrobacterium* with a Ti plasmid encoding a heterologous protein, infecting plant cells with the *Agrobacterium*, allowing expression of the heterologous protein, and recovering the heterologous protein from the plant cells. In one embodiment, the protein produced is an endoglucanase.

15 Claims, 38 Drawing Sheets

(56) References Cited

OTHER PUBLICATIONS

Lindbo, John A., "High-Efficiency Protein Expression in Plants from Agroinfection-Compatible Tobacco Mosaic Virus Expression Vectors", BMC Biotechnology, vol. 7, No. 52, 2007, 11 pages.

Mallory et al., "The Amplicon-Plus System for High-Level Expression of Transgenes in Plants", Nature Biotechnology, vol. 20, Jun. 2002, pp. 622-625.

Plesha et al., "High-Level Transient Production of a Heterologous Protein in Plants by Optimizing Induction of a Chemically Inducible Viral Amplicon Expression System", Biotechnology Progress, vol. 23, No. 6, 2007, pp. 1277-1285.

Plesha et al., "Optimization of the Bioprocessing Conditions for Scale-Up of Transient Production of a Heterologous Protein in Plants Using a Chemically Inducible Viral Amplicon Expression System", Biotechnology Progress, vol. 25, No. 3, 2009, pp. 722-734.

Pruss et al., "Plant Viral Synergism: The Potyviral Genome Encodes a Broad-Range Pathogenicity Enhancer that Transactivates Replication of Heterologous Viruses", The Plant Cell, vol. 9, Jun. 1997, pp. 859-868.

Sudarshana et al., "A Chemically Inducible Cucumber Mosaic Virus Amplicon System for Expression of Heterologous Proteins in Plant Tissues", Plant Biotechnology Journal, vol. 4, 2006, pp. 551-559.

\* cited by examiner

```
---------- RAmy3D signal Peptide ----------
MKNTSSLCLLLVLVLCSLTCNSGQAAGGGYWHTSGREILD
ANNVPVRIAGINWFGFETCNYVVHGLWSRDYRSMLDQIKSL
GYNTIRLPYSDDILKPGTMPNSINFYQMNQDLQGLTSLQVM
DKIVAYAGQIGLRIILDRHRPDCSGQSALWYTSSVSEATWIS
DLQALAQRYKGNPTVVGFDLHNEPHDPACWGCGDPSIDW
RLAAERAGNVLSVNPNLLIFVEGVQSYNGDSYWWGGNLQG
AGQYPVVLNVPNRLVYSAHDYATSVYPQTWFSDPTFPNNM
PGIWNKNWGYLFNQNIAPVWLGEFGTTLQSTTDQTWLKTL
VQYLRPTAQYGADSFQWTFWSWNPDSGDTGGILKDDWQT
VDTVKDGYLAPIKSSIFDPVGASPSSQPSVSPSPSP
SASRTPTPTPTPTASPTPTILTPTATPTPTASPTPSPTAASGA
RCTASYQVNSDWGNGFTVTVAVTNSGSVATKTWTVSWTF
GGNQTTTNSWNAAVTQNGQSVTARNMSYNNVIQPGQNTTF
GFQASYTGSNAAPTVACAAS──His-Tag──

E1 – β1,4-endoglucanase from *Acidothermus cellulolyticus*
```

Figure 2

CMVva (*Cucumber mosaic virus* amplicon expression system)

* *Bromoviridae* family, *Cucumovirus* genus
* Wide host range: Infects >1000 species of plants in 365 genera of 85 families, systemically infects cucumbers, tobaccos etc.

RNA1
m7GpppG — methyltransferase — helicase-like

RNA2
m7GpppG — RNA dependent RNA polymerase — 2b long distance movement protein and suppressor of PTGS RNA3
m7GpppG — movement protein RNA4
m7GpppG — coat protein

Figure 14

Modified RNA 4 leader sequences wt gttagtgtcactgactgactgactgtcgttcgttcagtggcct +

2+ <u>Eco RI</u>   <u>Nar I</u>   <u>Eco RI</u>   <u>Spe I</u>   <u>Eco RI</u>
   GAATTCGTGTAAGGCGCCGAATTCACTAGTGATTCGAGAGAATTC
                    <u>Not I</u>
                    <u>Pst I</u>

6+ <u>Eco RI</u>   <u>Nar I</u>   <u>Eco RI</u>   <u>Spe I</u>   <u>Hind III</u>
   GAATTCGTGTAAGGCGCCGAATTCACTAGTGATTCGAGAGAAGCTT
                    <u>Not I</u>
                    <u>Pst I</u>

8+ <u>Eco RI</u>   <u>Hind III</u>
   GAATTCGTGTAAGGCGAATTCTGCAGAAGCTT
                    <u>Pst I</u>

Figure 17

Other approaches to improve E1 expression

1. Systemic expression of CMV CP *in trans*

2. Subgroup I replicase complex containing RNA1 and RNA2 including 2b

3. C-terminal 33 amino acid deletion of the movement protein. For cell-to-cell movement, wild type CMV needs both the MP and CP. However, without the MP C-terminal 33 amino acids, CMV can move cell-to-cell without the CP. Thus it is possible that the tripartite replicating system might give increased endoglucanse due to cell-to-cell movement.

Figure 22

B) Secondary Structure of Modified RNA4 Leader Sequences

SEQUENCE LISTING

```
<160> NUMBER OF SEQ ID NOS: 5

<210> SEQ ID NO 1
<211> LENGTH: 551
<212> TYPE: PRT
<213> ORGANISM: A. cellulolyticus

<400> SEQUENCE: 1

Met Lys Asn Thr Ser Ser Leu Cys Leu Leu Leu Val Val Leu Cys
1               5                   10                  15

Ser Leu Thr Cys Asn Ser Gly Gln Ala Ala Gly Gly Gly Tyr Trp His
                20                  25                  30

Thr Ser Gly Arg Glu Ile Leu Asp Ala Asn Asn Val Pro Val Arg Ile
            35                  40                  45

Ala Gly Ile Asn Trp Phe Gly Phe Glu Thr Cys Asn Tyr Val Val His
        50                  55                  60

Gly Leu Trp Ser Arg Asp Tyr Arg Ser Met Leu Asp Gln Ile Lys Ser
65                  70                  75                  80

Leu Gly Tyr Asn Thr Ile Arg Leu Pro Tyr Ser Asp Asp Ile Leu Lys
                85                  90                  95

Pro Gly Thr Met Pro Asn Ser Ile Asn Phe Tyr Gln Met Asn Gln Asp
            100                 105                 110

Leu Gln Gly Leu Thr Ser Leu Gln Val Met Asp Lys Ile Val Ala Tyr
        115                 120                 125

Ala Gly Gln Ile Gly Leu Arg Ile Ile Leu Asp Arg His Arg Pro Asp
    130                 135                 140

Cys Ser Gly Gln Ser Ala Leu Trp Tyr Thr Ser Ser Val Ser Glu Ala
145                 150                 155                 160

Thr Trp Ile Ser Asp Leu Gln Ala Leu Ala Gln Arg Tyr Lys Gly Asn
                165                 170                 175

Pro Thr Val Val Gly Phe Asp Leu His Asn Glu Pro His Asp Pro Ala
```

```
                180                 185                 190
Cys Trp Gly Cys Gly Asp Pro Ser Ile Asp Trp Arg Leu Ala Ala Glu
            195                 200                 205

Arg Ala Gly Asn Val Leu Ser Val Asn Pro Asn Leu Leu Ile Phe Val
        210                 215                 220

Glu Gly Val Gln Ser Tyr Asn Gly Asp Ser Tyr Trp Trp Gly Gly Asn
225                 230                 235                 240

Leu Gln Gly Ala Gly Gln Tyr Pro Val Val Leu Asn Val Pro Asn Arg
            245                 250                 255

Leu Val Tyr Ser Ala His Asp Tyr Ala Thr Ser Val Tyr Pro Gln Thr
        260                 265                 270

Trp Phe Ser Asp Pro Thr Phe Pro Asn Asn Met Pro Gly Ile Trp Asn
        275                 280                 285

Lys Asn Trp Gly Tyr Leu Phe Asn Gln Asn Ile Ala Pro Val Trp Leu
        290                 295                 300

Gly Glu Phe Gly Thr Thr Leu Gln Ser Thr Thr Asp Gln Thr Trp Leu
305                 310                 315                 320

Lys Thr Leu Val Gln Tyr Leu Arg Pro Thr Ala Gln Tyr Gly Ala Asp
            325                 330                 335

Ser Phe Gln Trp Thr Phe Trp Ser Trp Asn Pro Asp Ser Gly Asp Thr
            340                 345                 350

Gly Gly Ile Leu Lys Asp Asp Trp Gln Thr Val Asp Thr Val Lys Asp
        355                 360                 365

Gly Tyr Leu Ala Pro Ile Lys Ser Ser Ile Phe Asp Pro Val Gly Ala
        370                 375                 380

Ser Ala Ser Pro Ser Ser Gln Pro Ser Pro Ser Val Ser Pro Ser Pro
385                 390                 395                 400

Ser Pro Ser Pro Ser Ala Ser Arg Thr Pro Thr Pro Thr Pro Thr Pro
            405                 410                 415

Thr Ala Ser Pro Thr Pro Thr Leu Thr Pro Ala Thr Pro Thr Pro
            420                 425                 430

Thr Ala Ser Pro Thr Pro Ser Pro Thr Ala Ser Gly Ala Arg Cys
        435                 440                 445

Thr Ala Ser Tyr Gln Val Asn Ser Asp Trp Gly Asn Gly Phe Thr Val
        450                 455                 460

Thr Val Ala Val Thr Asn Ser Gly Ser Val Ala Thr Lys Thr Trp Thr
465                 470                 475                 480

Val Ser Trp Thr Phe Gly Gly Asn Gln Thr Ile Thr Asn Ser Trp Asn
                485                 490                 495

Ala Ala Val Thr Gln Asn Gly Gln Ser Val Thr Ala Arg Asn Met Ser
            500                 505                 510

Tyr Asn Asn Val Ile Gln Pro Gly Gln Asn Thr Thr Phe Gly Phe Gln
        515                 520                 525

Ala Ser Tyr Thr Gly Ser Asn Ala Ala Pro Thr Val Ala Cys Ala Ala
        530                 535                 540

Ser His His His His His His
545                 550

<210> SEQ ID NO 2
<211> LENGTH: 53
<212> TYPE: DNA
<213> ORGANISM: A. cellulolyticus

<400> SEQUENCE: 2
```

```
gtttagttgt tcacctgagt cgtgttttct ttgttttgcg tctcagtgtg cct            53
```

```
<210> SEQ ID NO 3
<211> LENGTH: 62
<212> TYPE: DNA
<213> ORGANISM: Artificial Sequence
<220> FEATURE:
<223> OTHER INFORMATION: Synthetic Construct

<400> SEQUENCE: 3
gattcgtgta agggcgaatt ctgcaggcgg ccgcgaattc actagtgatt ctgagagaat    60
tc                                                                   62

<210> SEQ ID NO 4
<211> LENGTH: 63
<212> TYPE: DNA
<213> ORGANISM: Artificial Sequence
<220> FEATURE:
<223> OTHER INFORMATION: Synthetic Construct

<400> SEQUENCE: 4
gaattcgtgt aagggcgaat tctgcaggcg gccgcgaatt cactagtgat tctgagaaag    60
ctt                                                                  63

<210> SEQ ID NO 5
<211> LENGTH: 33
<212> TYPE: DNA
<213> ORGANISM: Artificial Sequence
<220> FEATURE:
<223> OTHER INFORMATION: Synthetic Construct

<400> SEQUENCE: 5
gaattcgtgt aagggcgaat tctgcagaag ctt                                 33
```

US 8,993,839 B2

PLANT-BASED PRODUCTION OF HETEROLOGOUS PROTEINS

CROSS-REFERENCE TO RELATED APPLICATIONS

This application claims the benefit of U.S. Provisional Application 61/399,904, filed Jul. 19, 2010, and U.S. Provisional Application 61/399,905, filed Jul. 19, 2010, the contents of which are hereby incorporated by reference in their entirety.

STATEMENT REGARDING FEDERALLY SPONSORED RESEARCH

This invention was made with government support under contracts 0653984 and 0948021 both awarded by the National Science Foundation. The government has certain rights in the invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 514112004500SubSeqList.txt, date recorded: Jul. 2, 2014, size: 6 KB).

BACKGROUND

1. Field

The present disclosure relates generally to plant-based production of heterologous proteins, and more specifically to the in planta production of heterologous proteins.

2. Description of the Related Art

Biofuels such as ethanol are fermented from glucose, and the cellulose in biomass is a potential source of this sugar. However, a synergistic set of enzymes is needed to degrade the cellulose into glucose. Typically, these enzymes are produced by fungal cell culture which requires a high capital cost and a large number of bioreactors. Thus, there is a need for a more efficient system of enzyme production that requires lower capital costs, expends less energy, and emits less carbon dioxide.

BRIEF SUMMARY

The compositions and methods of this disclosure address this need by facilitating the high-yield, low-cost in planta production of heterologous proteins, such as cellulases. In planta production of cell wall degrading enzymes may alleviate the need for costly and energy-intensive production of purified cellulase for biomass fermentation and thereby help to lower production costs and improve the energy balance of biofuel manufacturing processes. Specifically, the present disclosure provides for plant virus-based systems enabling the transient in planta expression of heterologous proteins, such as cellulases. The present disclosure further provides methods of using such plant virus based expression systems to produce high yields of heterologous proteins in plants.

One aspect of the present disclosure provides for a plant cell capable of expressing a heterologous protein, whereby the plant cell includes a complete viral amplicon that is encoded by more than one plasmid. This amplicon includes multiple amplicon segments. The amplicon is capable of amplifying the transcription of a nucleic acid sequence that encodes the heterologous protein of interest. The amplicon includes at least two plasmids, whereby the first plasmid is different from the second plasmid. The first plasmid includes at least one amplicon segment containing a nucleic acid sequence that encodes the heterologous protein and the second plasmid includes at least one amplicon segment.

In some embodiments the viral amplicon is a cucumovirus amplicon and in specific embodiments the amplicon is a Cucumber Mosaic Virus (CMV) amplicon.

In some embodiments, the viral amplicon is a bipartite system that is encoded by two plasmids. In a preferred embodiment the first plasmid includes the CMV RNA 3 amplicon segment, whereby RNA 3 includes a nucleic acid sequence encoding the heterologous protein. In another preferred embodiment the second plasmid includes the CMV RNA 1 and RNA 2 amplicon segments. In some specific embodiments the second plasmid includes a promoter sequence that is responsive to a chemical inducer and operably linked to a nucleic acid sequence encoding a viral protein. In some specific embodiments the chemical inducer is estradiol or methoxyfenozide. In some specific embodiments the viral protein is a replicase or a replicase subunit. In some specific embodiments the second plasmid includes a Kanamycin selection marker and the first plasmid does not include a Kanamycin selection marker.

In some embodiments the viral amplicon is a tripartite system that is encoded by three plasmids. In a preferred embodiment the first plasmid includes the CMV RNA 3 amplicon segment, whereby RNA 3 includes a nucleic acid sequence encoding the heterologous protein. In another preferred embodiment the second plasmid includes the CMV RNA 1 amplicon segment and the third plasmid includes the CMV RNA 2 amplicon segment.

Another aspect of the current disclosure provides for a plant cell capable of expressing a heterologous protein, whereby the plant cell includes a complete viral amplicon that includes amplicon segments from more than one viral subgroup.

In a preferred embodiment the viral amplicon is a CMV amplicon, the amplicon segment RNA 3 is from a CMV subgroup II strain and the amplicon segments RNA 1 and RNA 2 are from a CMV subgroup I strain, such as a California subgroup I strain.

In some embodiments the CMV RNA 3 amplicon segment includes a RNA 4 segment that has a modified 5'-leader sequence containing more restriction enzyme sites than the corresponding wild-type RNA 4 5'-leader sequence.

In some embodiments the heterologous protein is a secreted protein. In other embodiments the heterologous protein is GFP or RFP. In other embodiments the heterologous protein is an enzyme capable of modifying, degrading, or decomposing plant cell walls. In some specific embodiments the enzyme has optimal activities at temperatures >30° C. In some specific embodiments the enzyme is a cellulase. In some specific embodiment the cellulase is an endoglucanase, an exoglucanase, a β-glucosidase, or a xylanase. In a preferred embodiment the endoglucanase is the E1 β-1,4-endoglucanase from *Acidothermus cellulolyticus*. In some embodiments the amplicon segment that includes the nucleic acid sequence encoding the heterologous protein further includes a CaM 35S promoter that is operably linked to the nucleic acid sequence encoding the heterologous protein.

The plant cell may form part of a cell culture, an excised plant tissue, or an intact plant. In some embodiments the plant cell is a tobacco, switchgrass, miscanthus, sunflower, sugar pumpkin, or squash plant cell. In a specific embodiment the plant cell is a *Nicotiana benthamiana* cell.

In some embodiments the plant cell also includes a cDNA encoding a gene silencing suppressor. In some embodiment the gene silencing suppressor is an RNA-silencing suppressor (RSS). In some embodiments the RSS is the helper-component proteinase HC-Pro. In some embodiments the gene silencing suppressor is from Tomato Bushy Stunt Virus (TBSV) or Tobacco Etch Virus (TEV). In some embodiments the plant cell is a transgenic plant cell expressing elevated levels of a gene silencing suppressor compared to a wild-type plant cell. In some embodiments the viral amplicon can replicate in planta and move systemically. In some specific embodiments the plant cell includes a cDNA encoding a mutant form of the CMV 3a movement protein. In a preferred embodiments the mutant form of the CMV 3a movement protein includes a 33 amino acid C-terminal deletion Another aspect of the current disclosure provides for a method for producing a heterologous protein by: i) contacting a plant cell, plant or excised plant tissue with a bacterial cell; this bacterial cell includes a complete viral amplicon, whereby the amplicon includes multiple amplicon segments, and the amplicon is capable of amplifying the transcription of a nucleic acid sequence that encodes the heterologous protein; ii) allowing for a sufficient time to produce the heterologous protein in the plant cell; and iii) harvesting at least 0.5 milligrams of the heterologous protein per kilogram of fresh weight of the plant cell, plant, or excised plant tissue. In some embodiments the at least 0.5 milligrams are at least 1.0 milligrams. In some embodiments the at least 1.0 milligrams are at least 1.5 milligrams. In some embodiments the at least 1.5 milligrams are at least 2.0 milligrams. In some embodiments the at least 2.0 milligram are at least 3.0 milligram. In some embodiments the at least 3.0 milligram are at least 4.0 milligram.

Another aspect of the current disclosure provides for a method for producing a heterologous protein by: i) contacting a plant cell with at least one plant hormone; ii) contacting the plant cell with a bacterial cell; this bacterial cell includes a complete viral amplicon, whereby the amplicon includes multiple amplicon segments, and the amplicon is capable of amplifying the transcription of a nucleic acid sequence that encodes the heterologous protein; iii) allowing for a sufficient time to produce the heterologous protein in the plant cell; and iv) harvesting the heterologous protein produced by the plant cell.

In some embodiments the at least one plant hormone is at least two plant hormones. In some embodiments the at least one plant hormone is selected from the group consisting of jasmonic acid, gibberellin A3, indole acetic acid, 2,4-dichlorophenoxyacetic acid, kinetin, and salicylic acid.

Another aspect of the current disclosure provides for a method for producing a heterologous protein by: i) mechanically wounding a plant or excised plant tissue; ii) contacting the plant or excised plant tissue with a bacterial cell; this bacterial cell includes a complete viral amplicon, wherein the amplicon includes multiple amplicon segments, whereby the amplicon is capable of amplifying the transcription of a nucleic acid sequence that encodes the heterologous protein; ii) allowing for a sufficient time to produce the heterologous protein in the plant cell; and iii) harvesting the heterologous protein produced by the plant cell. In some embodiments the plant or excised plant tissue is mechanically wounded by pressing the plant or excised plant tissue with a brush.

Another aspect of the current disclosure provides for a method for producing a heterologous protein by: i) contacting the plant cell with a bacterial cell at a first temperature, whereby the bacterial cell includes a complete viral amplicon and the amplicon includes multiple amplicon segments and is capable of amplifying the transcription of a nucleic acid sequence encoding the heterologous protein; ii) incubating the plant cell at a second temperature for a sufficient time to produce the heterologous protein in the plant cell; and iii) harvesting the heterologous protein produced by the plant cell. In some embodiments the first temperature is 20° C. and the second temperature is 26° C. or 30° C.

In some embodiments the heterologous protein is produced transiently in the plant cell, plant or excised plant tissue. In some embodiments contacting the plant cell, plant or excised plant tissue is conducted by pressure infiltration or vacuum infiltration. In some embodiments four days are a sufficient time to produce the heterologous protein in the plant cell, plant or excised plant tissue. In other embodiments six days are a sufficient time. In a preferred embodiment the first and second bacterial cells are *Agrobacterium tumefaciens* cells.

In some embodiments the method includes the additional step of contacting the bacterial cell with a chemical inducer. In some embodiments the method includes the additional step of contacting the plant cell, plant or excised plant tissue with a second bacterial cell that includes a recombinant nucleic acid sequence encoding a gene silencing suppressor or a viral coat protein. In some embodiments the method includes the additional step of activating the heterologous protein in situ, whereby protein activation results in the degradation of the plant cell walls. In some embodiments the method includes the additional step of removing the soluble components of the plant or excised plant tissue apoplast by apoplast washing.

BRIEF DESCRIPTION OF THE DRAWINGS

FIG. 2 depicts the expected amino acid sequence from the β-1,4-endoglucanase translation product (SEQ ID NO:1).

FIG. 14 depicts the CMVva expression system that includes RNA 1, RNA 2, RNA 3, and RNA 4.

FIG. 17 depicts the modified RNA 4 leader sequences: wt (SEQ ID NO:2), 2+ (SEQ ID NO:3), 6+ (SEQ ID NO:4), 8+ (SEQ ID NO:5). Modified RNA 4 leaders were used to enhance expression of CMV coat protein and other inserted sequences (GFP, endoglucanase).

FIG. 22 depicts other approaches to improve E1 expression.

DETAILED DESCRIPTION

The following description sets forth numerous exemplary configurations, parameters, and the like. It should be recognized, however, that such description is not intended as a limitation on the scope of the present invention, but is instead provided as a description of exemplary embodiments.

1. Selection of Heterologous Proteins

*A. cellulolyticus* is a thermophilic bacterium that lives in high-temperature, acidic environments, such as the hot springs of Yellowstone National Park. Enzymes from thermophilic organisms often have optimal activities at temperatures >30° C. The β-1,4-endoglucanase E1 enzyme was selected from this organism as a preferred embodiment of a heterologous protein because its ability to hydrolyze cellulose is inhibited at ambient temperatures, so in planta expression of this gene does not alter the plant's phenotype. The enzyme is most active at high temperatures and low pH. The E1 endoglucanase has optimal activity at about 80° C. and pH 5.5, which is approximately the pH of the plant cell apoplast. The sequence for E1 was obtained from the NIH Entrez cross-database search (accession number P54583). The mature protein (without the native secretion signal peptide) consists of 521 amino acids with an estimated molecular weight of 56,477 Da. The protein consists of a catalytic domain (E1-cd, ~40.3 kDa) and a cellulose-binding domain (E1-cbd, ~10.8 kDa), connected by a linker region (E1-link, ~5.4 kDa). The 41-amino-acid native signal peptide was replaced by the 25-amino-acid signal peptide from *Oryza saliva* α-amylase (Ramy3D SP) to facilitate secretion of the protein from plant cells to the apoplast.

2. Codon Optimization, Gene Synthesis

Figure 1:
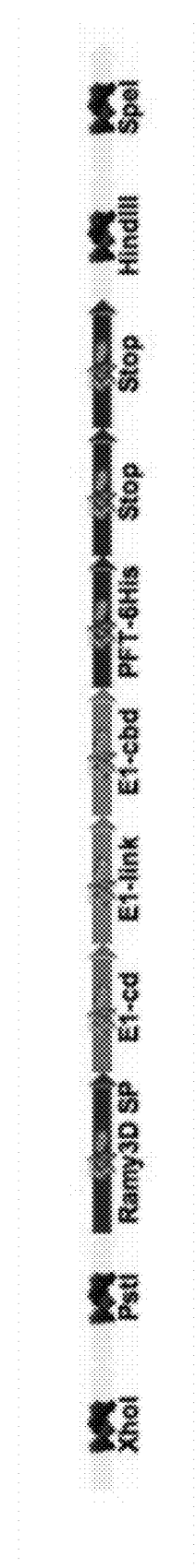
FIG. 1 depicts a schematic of the gene synthesized by DNA 2.0, Inc. RAMY 3D SP encodes a signal peptide from rice alpha amylase. E1 is β-1,4-endoglucanase E1 from *Acidothermus cellulolyticus*. E1-cd encodes the E1 catalytic domain. E1-link encodes the E1 linker domain. E1-cbd encodes the E1 cellulose binding domain. PFT-6His encodes a peptide fusion tag, a 6 polyhistidine tag. Stop codons and restriction enzyme sites (XhoI, PstI, HindIII, and SpeI) have been added to flanking regions.

The gene for *A. cellulolyticus* β-1,4-endoglucanase E1 was codon-optimized for expression in *N. benthamiana* using the codon usage table for this plant from the KEGG database. A polyhistidine tag was added to the C-terminus of the protein to allow rapid purification by metal affinity chromatography. Appropriate restriction enzyme sites were added to allow insertion into our other expression cassettes. The entire 1,566 bp DNA fragment was chemically synthesized by an outside company (DNA 2.0, Inc., Menlo Park, Calif.) (FIG. 1).

3. Cloning into Binary Expression Vectors

The chemically synthesized E1 gene that encodes β-1,4-endoglucanase from *A. cellulolyticus* was provided by DNA 2.0 in the vector pJ210:11772. The coding region of 552aa protein shown in FIG. 2 contains the 25aa Ramy3D signal peptide fused to the N-terminal and a 6aa his-tag at the C-terminal.

4. Cloning into the 35S Expression Vector (for Constitutive Expression)

Figure 3:
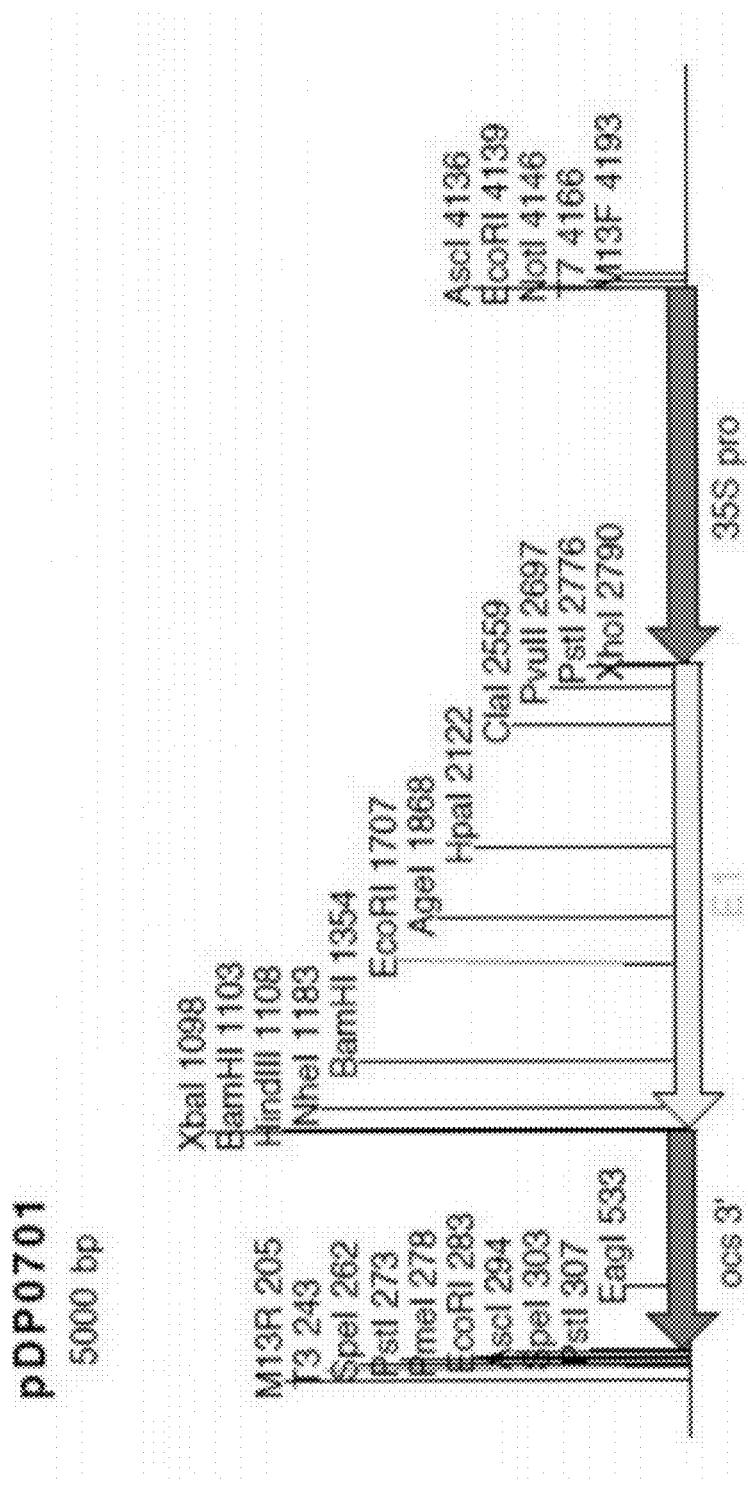
FIG. 3 depicts a map of the pDP0701 vector.
Figure 4:
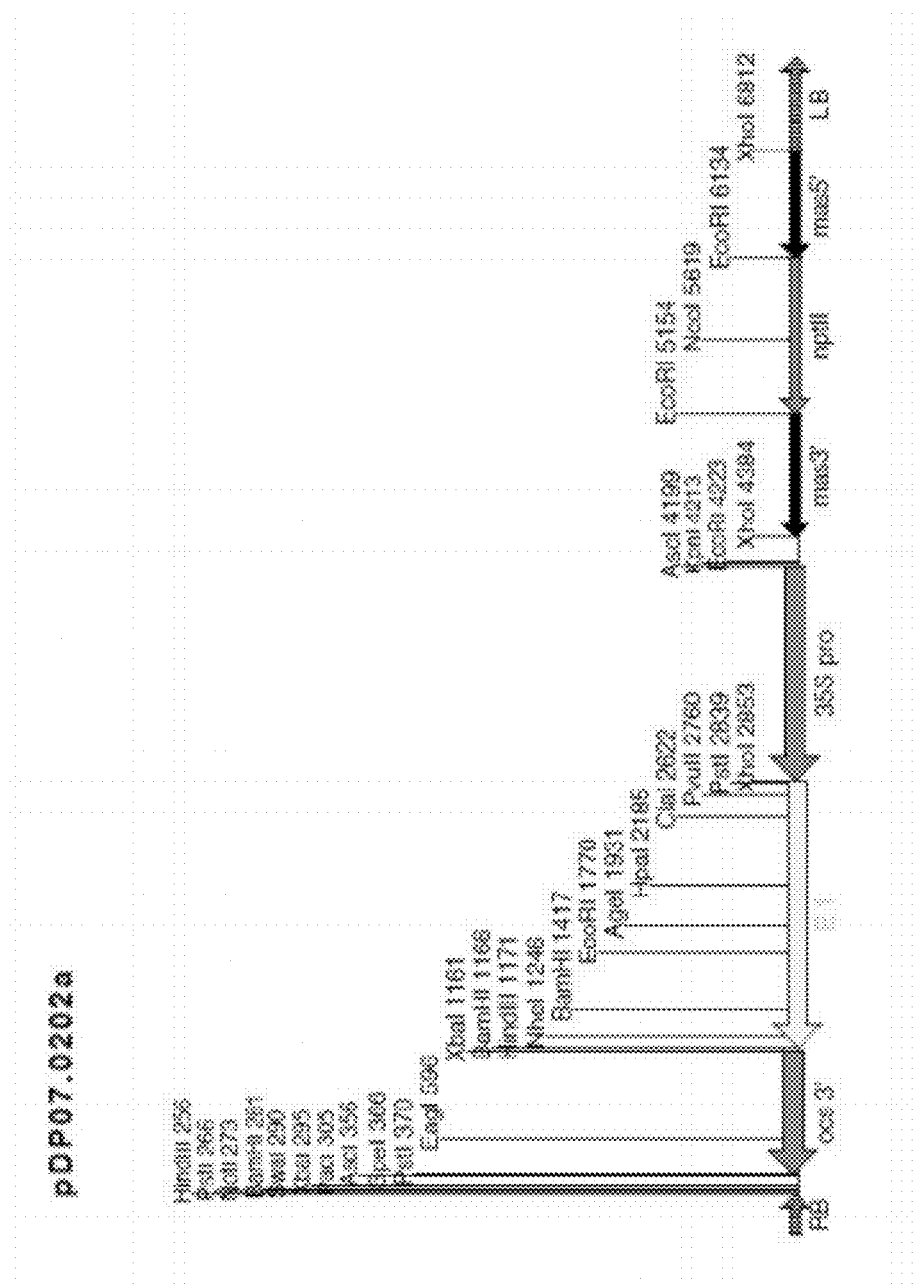
FIG. 4 depicts a map of the pDP07.0202a binary vector.

The vector pJ210:11772 containing E1 was digested with the restriction endonucleases XhoI and HindIII at positions 1198 and 2872 respectively yielding a 1674 bp fragment that was directionally cloned into the shuttle vector pDE00.0113 creating the plasmid pDP0701. The E1 coding region was cloned downstream from a 35S promoter and upstream from an ocs3' regulatory sequence creating an E1 35S expression cassette. The E1 expression cassette in pDP0701 (FIG. 3) was excised by digestion with the endonuclease AscI and inserted into the binary vector pDU97.1005 creating the vector designated pDP07.0202a (FIG. 4).

5. Creation of Recombinant *Agrobacterium* Strains Containing the 35S Expression Cassette The binary plasmid pDP07.0202a was electroporated into the following two *Agrobacterium* strains, EHA105 pCH32 and C58C1, resulting in two recombinant *Agrobacterium tumefaciens* (*A. tumefaciens*) strains that can be used to transiently express the E1 protein in plant systems.

6. Production of Recombinant Cellulase Enzyme Using Transient Agroinfiltration in *N. Benthamiana*

Figure 5:
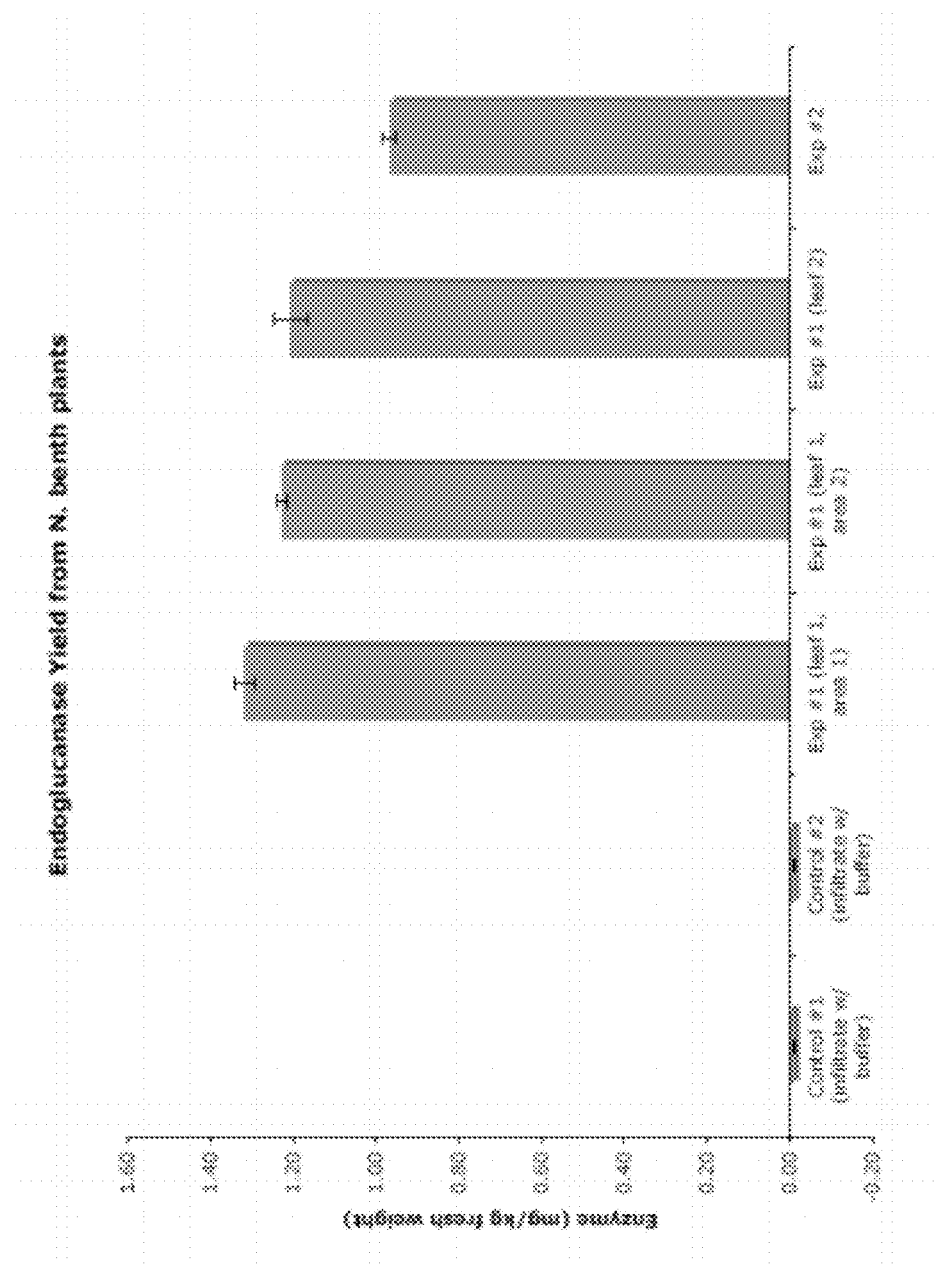
FIG. 5 depicts the amount of endoglucanase produced in various tissue samples from tobacco plants (*Nicotiana benthamiana*). Controls #1 and #2 are two different tobacco plants infiltrated with buffer but no bacteria. Experimental #1 and #2 are two different tobacco plants infiltrated with *Agrobacteria* suspended in buffer. Variability was examined between different areas of the same leaf and between leaves of experimental plant #1. Plant to plant variability was examined between experimental plants #1 and #2.

In the transient expression studies the recombinant EHA105 pCH32 Agrobacterial strain with the constitutive CaMV 35S promoter was used. In this expression system, the E1 transcript is produced under the control of the strong 35S constitutive promoter. This strain of bacteria was cultured in the lab and used to infect four-week-old tobacco (*N. benthamiana*) plants. Infection could take place in the presence or absence of a gene silencing suppressor. The leaves of a 4 week old *N. benthamiana* plant were vacuum infiltrated. After four days, plant tissue was harvested, homogenized, extracted and tested for enzyme activity. Results are summarized in FIG. 5. The minimum amount of enzyme expressed after 4 days was approximately 1 mg cellulase per kg fresh plant cell weight. The activity corresponding to the amounts of enzyme shown in FIG. 5 ranged from 40,000 to 52,000 nmol MU/min/kg fresh plant tissue weight at pH 5.5 and at 65° C.

This experiment demonstrated a proof of principle that *A. tumefaciens* can be used to transiently (and rapidly) produce functional endoglucanase in plant tissue. Variability was observed between different tissues and different plants, but in general the yield was 1 mg of enzyme/kg fresh plant weight. Similar results were seen with this constitutive promoter for production of a different protein (human AAT) using this method (Sudarshana et al. *Plant Biotech J.* 4: 551-559 (2006)). However, when a viral amplified expression system was used to express AAT, a 70-fold yield increase was achieved, so it is expected that substantial improvements in productivity may be seen when a viral amplicon expression system is used. Also, the activity assay was used to show that the *A. tumefaciens* itself does not produce the enzyme, the plant tissue does. It was also demonstrated that his-tagged rE1 at the C-terminal does not eliminate activity. Accordingly, one embodiment of the methods described herein is the functional production of rE1 via transient agroinfiltration in plant tissues.

Figure 6:
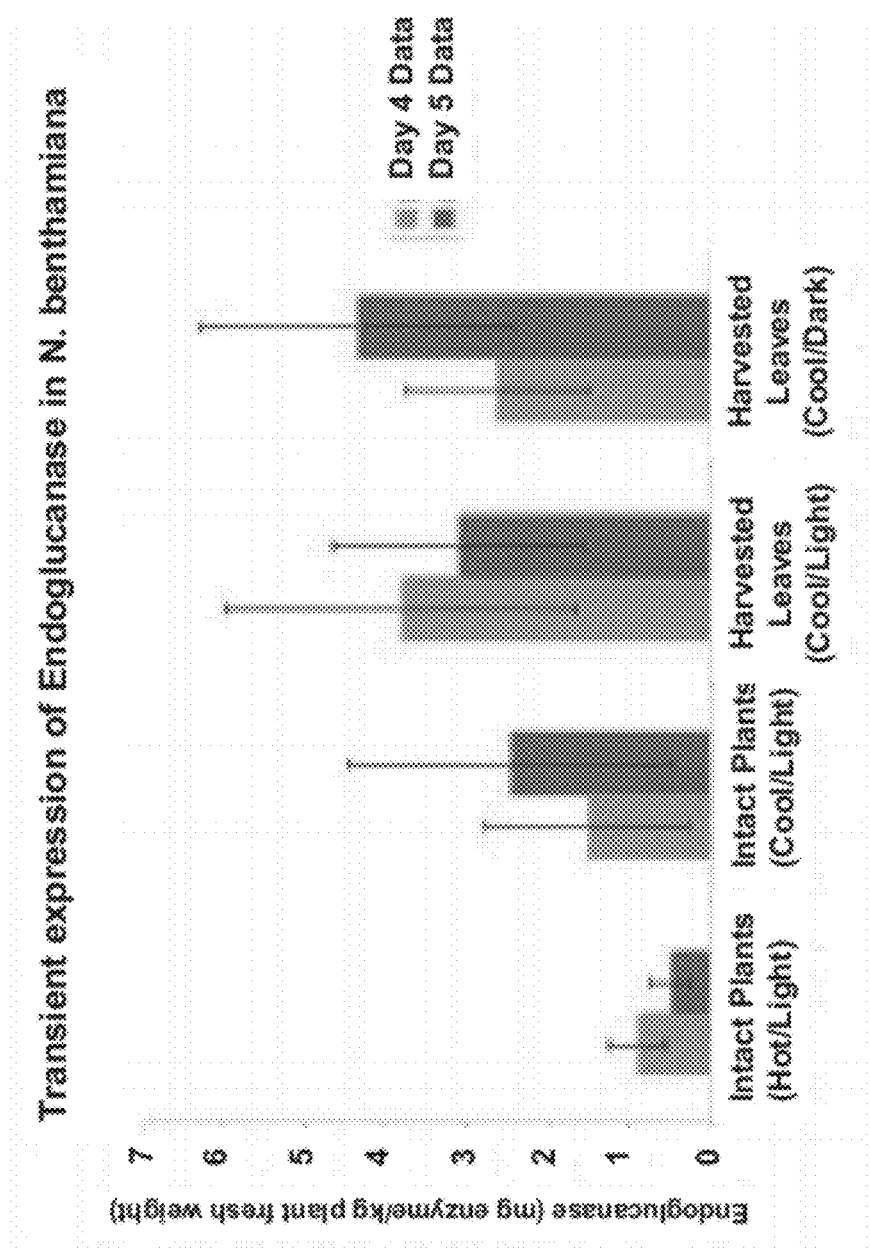
FIG. 6 depicts transient expression of endoglucanase in tobacco plants. The amount of endoglucanase was monitored over time in infiltrated intact plants and harvested leaves stored in different environments. Hot refers to maximum temperatures >30° C. Cool refers to maximum temperatures <30° C. Light refers to a 16 h/8 h light/dark cycle. Dark refers to 24 h darkness.
Figure 7:
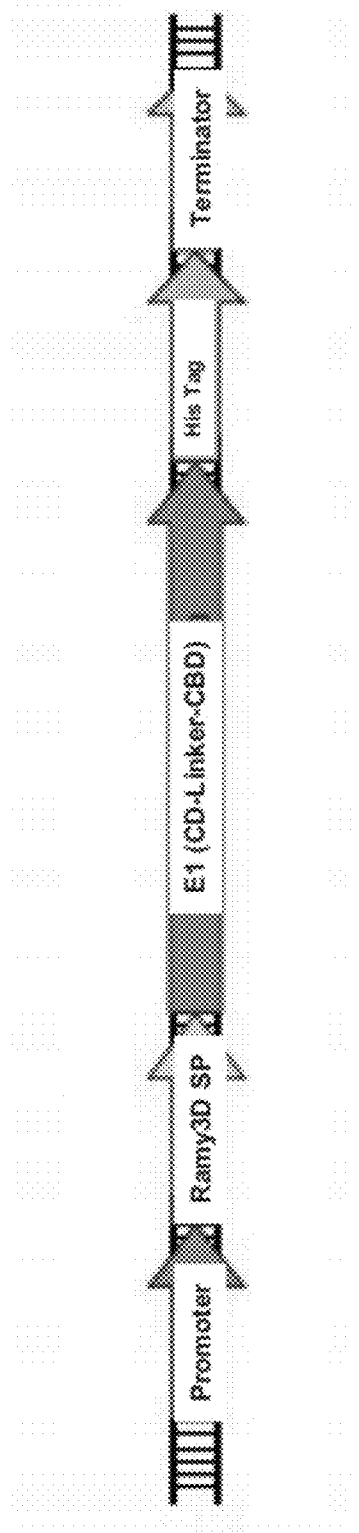
FIG. 7 depicts the modified gene for endoglucanase from *A. cellulolyticus*. The 35S promoter from Cauliflower Mosaic Virus facilitates constitutive transcription.
Figure 8:
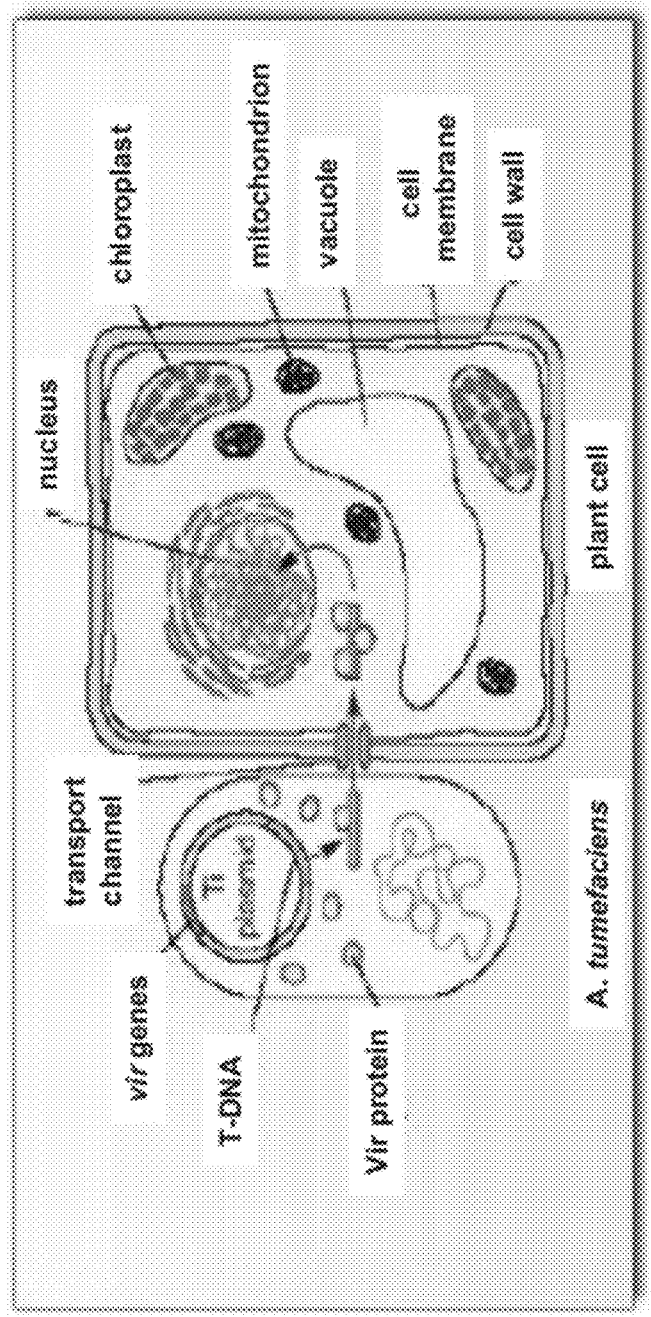
FIG. 8 depicts an *Agrobacterium* transferring a specific segment of its Ti plasmid into a plant cell.
Figure 9:
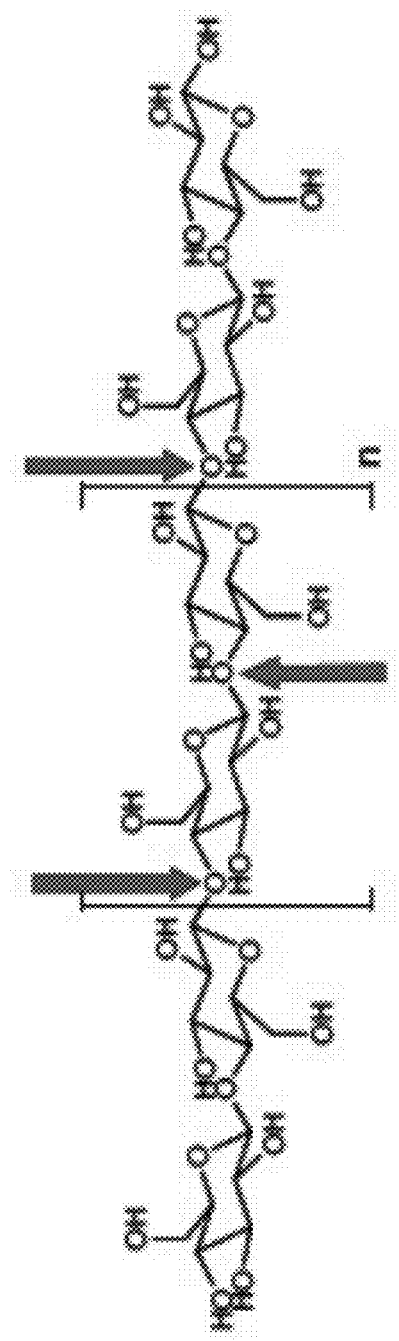
FIG. 9 depicts endoglucanase hydrolyzing β-1,4-glucosidic bonds within cellulose chains (arrows).
Figure 10:
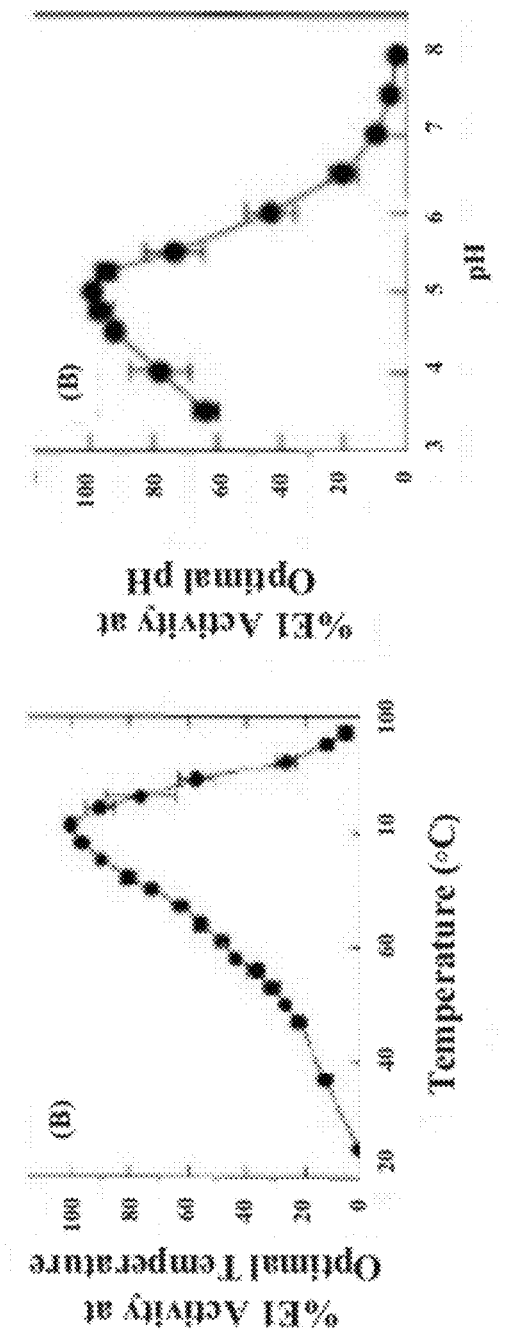
FIG. 10 depicts the optimal conditions for endoglucanase activity.
Figure 11:
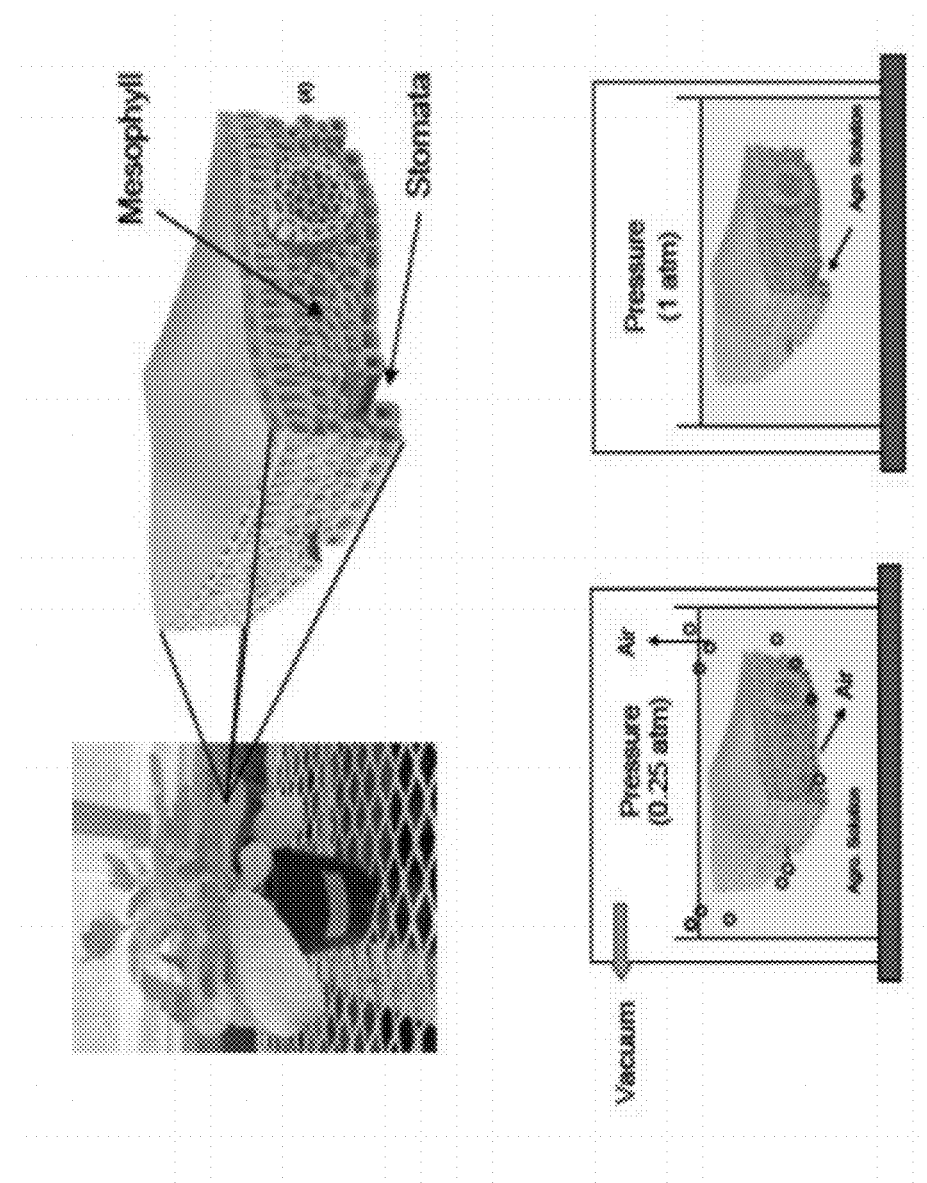
FIG. 11 depicts how vacuum infiltration brings *Agrobacteria* and plant cells together. The leaf tissue is immersed in a suspension of *Agrobacteria*, and a vacuum is pulled within the chamber. Air bubbles emerge from the leaf tissue and rise to the surface. The vacuum is released, and the liquid containing the *Agrobacteria* floods the tissue, bringing the bacteria in direct contact with the plant cells.
Figure 12:
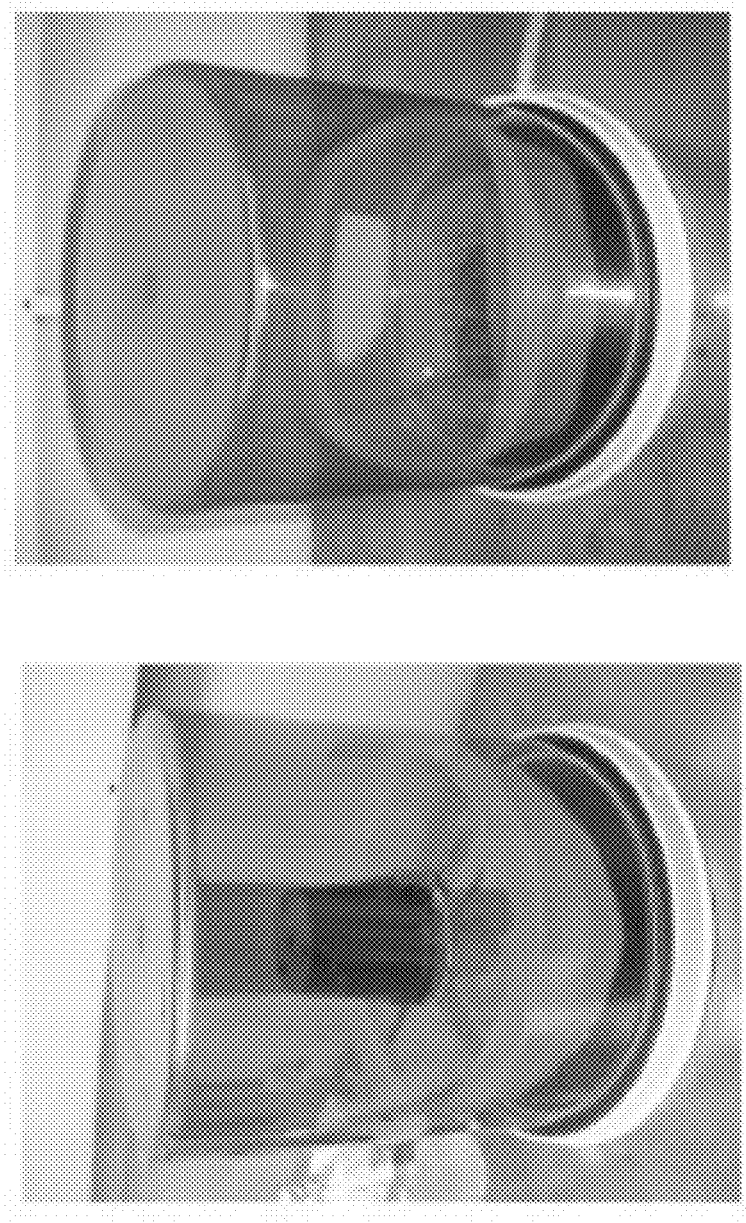
FIG. 12 depicts the lab-scale vacuum chamber used to infiltrate intact plants (left) or detached leaves (right).
Figure 13:
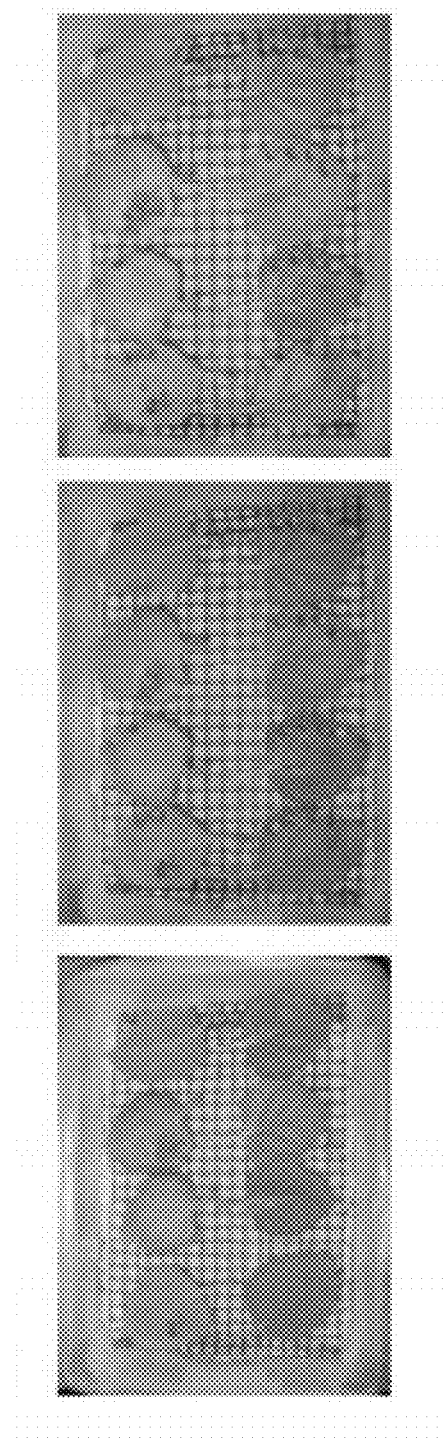
FIG. 13 depicts detached leaves 4 days (left), 6 days (middle), and 9 days (right) after infiltration with *Agrobacteria*.

It was also demonstrated that functional recombinant E1 can be produced in excised plant tissue, such as harvested *N. benthamiana* leaves, at even slightly higher expression levels (FIG. 6). In these transient expression studies, the EHA105 pCH32 agrobacterial strain was used with the constitutive CaMV 35S promoter. This strain of bacteria was cultured in the lab and used to infect four-week-old tobacco (*N. benthamiana*) plants. The leaves of a 4 week old *Nicotiana benthamiana* plant were vacuum infiltrated. After four days, plant tissue was harvested, homogenized, extracted and tested for enzyme activity. The infiltrated plants and leaves were stored at various conditions to determine their effect on enzyme yield. Intact plants were stored in a hot greenhouse (daily high temperatures >30° C., 14 hours of light per day). To keep the harvested leaves alive, they were stored in a humid container at a constant temperature of 22° C. and protected from light. To make a valid comparison between the plants and leaves, some of each were stored adjacent to each other indoors, at ~25° C. with 16 hours of light per day. The leaves were stored in a humid container with a clear covering to allow illumination. Intact plants and harvested leaves were tested for enzyme activity after four and six days of incubation. The average amount of enzyme expressed after 6 days was approximately 2.6 mg cellulase per kg fresh plant cell weight. Activity assay results were converted to expression level (mg E1/kg fresh weight plant tissue) based on the reported specific activity of native E1.

In a further embodiment, activation of the cellulase in planta allows for in situ degradation of cellulose within the leaf tissue. In a specific embodiment activation of the cellulose may include raising the temperature above 30° C. In another specific embodiment activation of the cellulase may include raising the temperature to about the temperature at which the cellulase has optimal enzyme activity.

Although this E1 embodiment involves the specific example of transient agroinfiltration of rE1 in *N. benthamiana* using a constitutive expression system (CaMV 35S promoter), the approach can be used for production of any heterologous protein.

Generally, heterologous proteins of this disclosure may include nonenzymatic proteins such as the green or red fluorescent proteins GFP or RFP, or viral coat proteins such as the CMV coat protein (CP). Alternatively, heterologous proteins may include enzymes, such as enzymes that are capable of modifying, degrading, or decomposing plant cell walls. For example, enzymes may include cellulose degrading enzyme, including, without limitation, other endoglucanases, exoglucanases, β-glucosidases, and xylanases. Additionally, multiple enzymes may be expressed in the same host plant using co-infiltration, different host plants may be used for protein production, and different promoters, plasmids, and expression systems may be employed. Heterologous proteins may be selected from various organisms, including, without limitation, *A. cellulolyticus*.

Generally, nucleic acid sequences encoding heterologous proteins of this invention may be codon optimized. The phrase "codon optimization" refers to the selection of appropriate DNA nucleotides for use within a structural gene or fragment thereof that approaches codon usage within the plant of interest. Therefore, an optimized gene or nucleic acid sequences refers to a gene in which the nucleotide sequence of a native or naturally occurring gene has been modified in order to utilize statistically-preferred or statistically favored codons within the plant. The nucleotide sequence typically is examined at the DNA level and the coding region optimized for expression in the plant species determined using any suitable procedure, for example as described in Sardana et al. (Plant Cell Reports 15, 677-81 (1996)).

7. Viral Amplicon Based Expression Systems for Production of Heterologous Proteins For purposes of this disclosure, the term "viral amplicon" is used to describe the minimal non-host cell genetic material required to amplify the transcription of a nucleic acid sequence in a host cell, whereby the nucleic acid sequence encodes a heterologous protein and promotes its expression in the host cell. Viral amplicons may be comprised of multiple segments, such as the chromosomal cucumovirus RNA segments RNA 1, RNA 2, or RNA 3. Viral amplicons may be encoded on a single plasmid or multiple plasmids, such as two or three plasmids. Within any given viral amplicon, individual amplicon segments may be selected and recombined from different virus families or subgroups, such as the Cucumber Mosaic Virus (CMV) subgroups I and II.

Viral amplicons may be selected from any plant virus, including the Bromoviridae Family of plant viruses and its six genera: Alfamovirus, exemplified by Alfalfa Mosaic Virus, Anulavirus, exemplified by Pelargonium Zonate Spot Virus, Bromovirus, exemplified by Brome Mosaic Virus, Cucumovirus, exemplified by Cucumber Mosaic Virus, Ilarvirus, exemplified by Tobacco Streak Virus, and Oleavirus, exemplified by Olive Latent Virus 2.

Recombinant CMV amplicons containing amplicon segments from more than one CMV subgroup were used to increase CMV coat protein, and heterologous gene (protein) expression in the CMV Viral Amplicon (CMVva) system (FIG. 14). The original CMVva system was developed by using specific CMV genomic segments for the CMV isolate Q, which is designated in the taxonomic CMV subgroup II. The CMV literature shows that CMV subgroup I isolates are more common and often more aggressive in plants, suggesting that they replicate to higher levels. Because CMV has three chromosomal RNA segments (RNA 1, RNA 2, and RNA 3), and because these can in some cases be mixed to create new reassortant CMV strains, a California CMV subgroup 1 strain was used to create complete cDNAs corresponding to all three chromosomal segments. A recombinant viral amplicon was thus created by mixing the CMV subgroup 1 amplicon segments RNA 1 and RNA 2 together with CMV subgroup II amplicon segment RNA 3. Segments RNA 1 and RNA 2 encode for replication-associated proteins and the host defense protein 2b, the silencing suppressor. Amplicon segment RNA 3 encodes for the 3a movement protein and the capsid protein. However, the subgroup II RNA 3 segment has been modified for insertion and expression of heterologous genes (proteins).

When the recombinant CMV amplicon was used for agroinfiltration and protein expression in *N. benthamiana* plants, the recombinant CMV amplicon gave higher levels of three proteins tested so far. These are the CMV coat protein, GFP and endoglucanase E1 (the latter was assessed by immunoblot analysis and for enzymatic activity).

Previous work using a monopartite expression system based on a single plasmid encoding the CMV amplicon was described in PCT publication WO 2008/036424 (published Mar. 27, 2008), which is hereby incorporated by reference, particularly with respect to CMV encoding plasmids and RNAs described therein.

Figure 15:
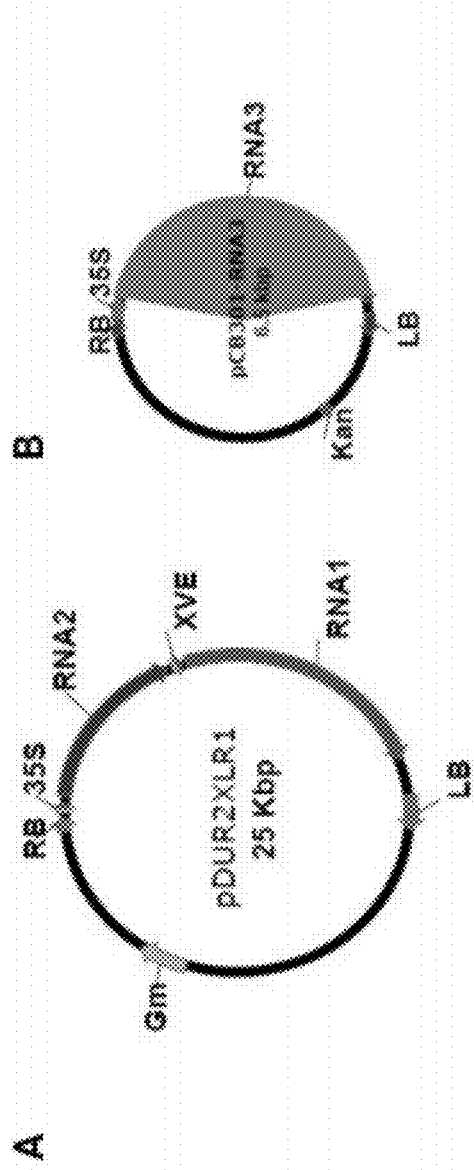
FIGS. 15A and 15B depict vector maps of the bipartite inducible system vectors: (A) pDUR2XLR1 and (B) pB301-RNA3.
Figure 16:
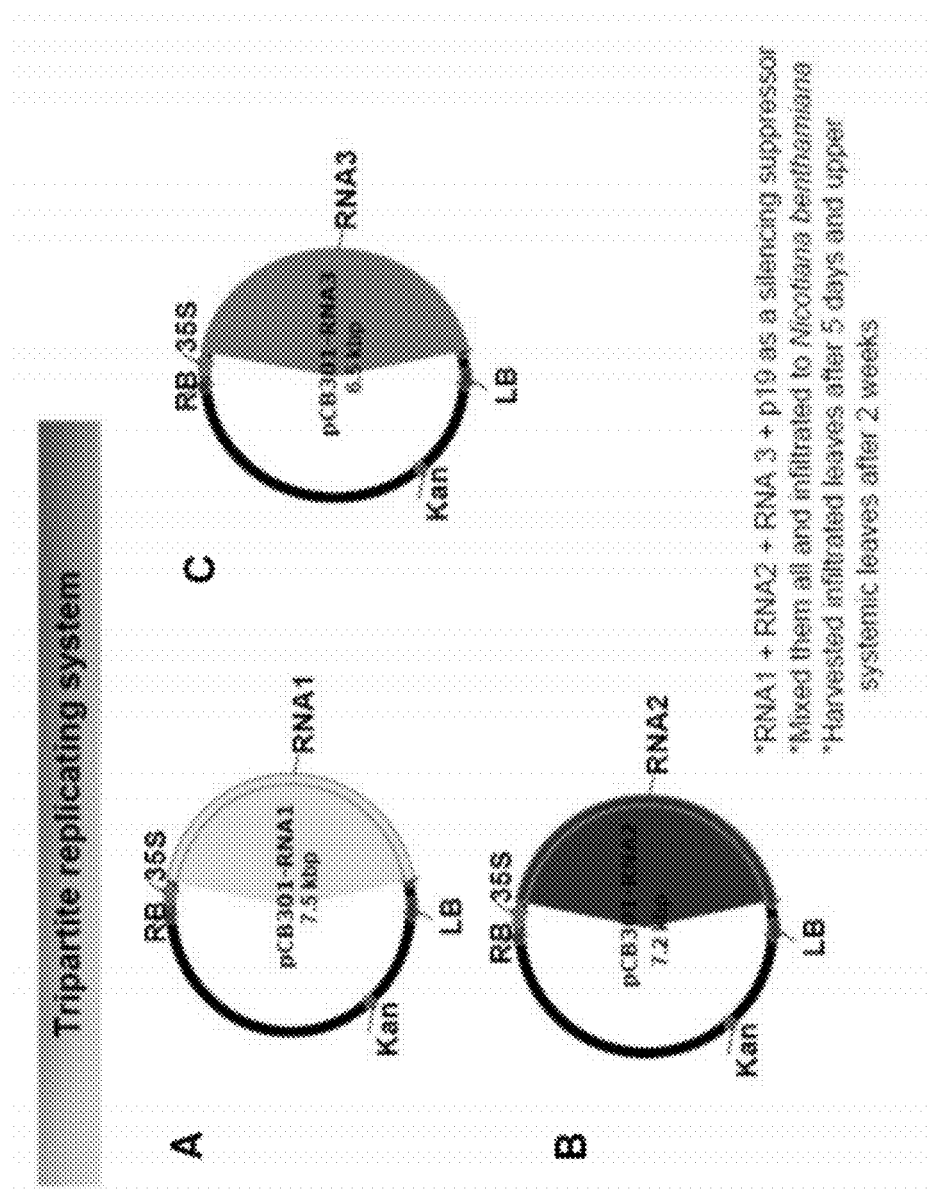
FIGS. 16A, 16B, and 16C depict vector maps of the tripartite replicating system vectors: (A) pCB301-RNA1; (B) pCB301-RNA2; and (C) pCB301-RNA3
Figure 18:
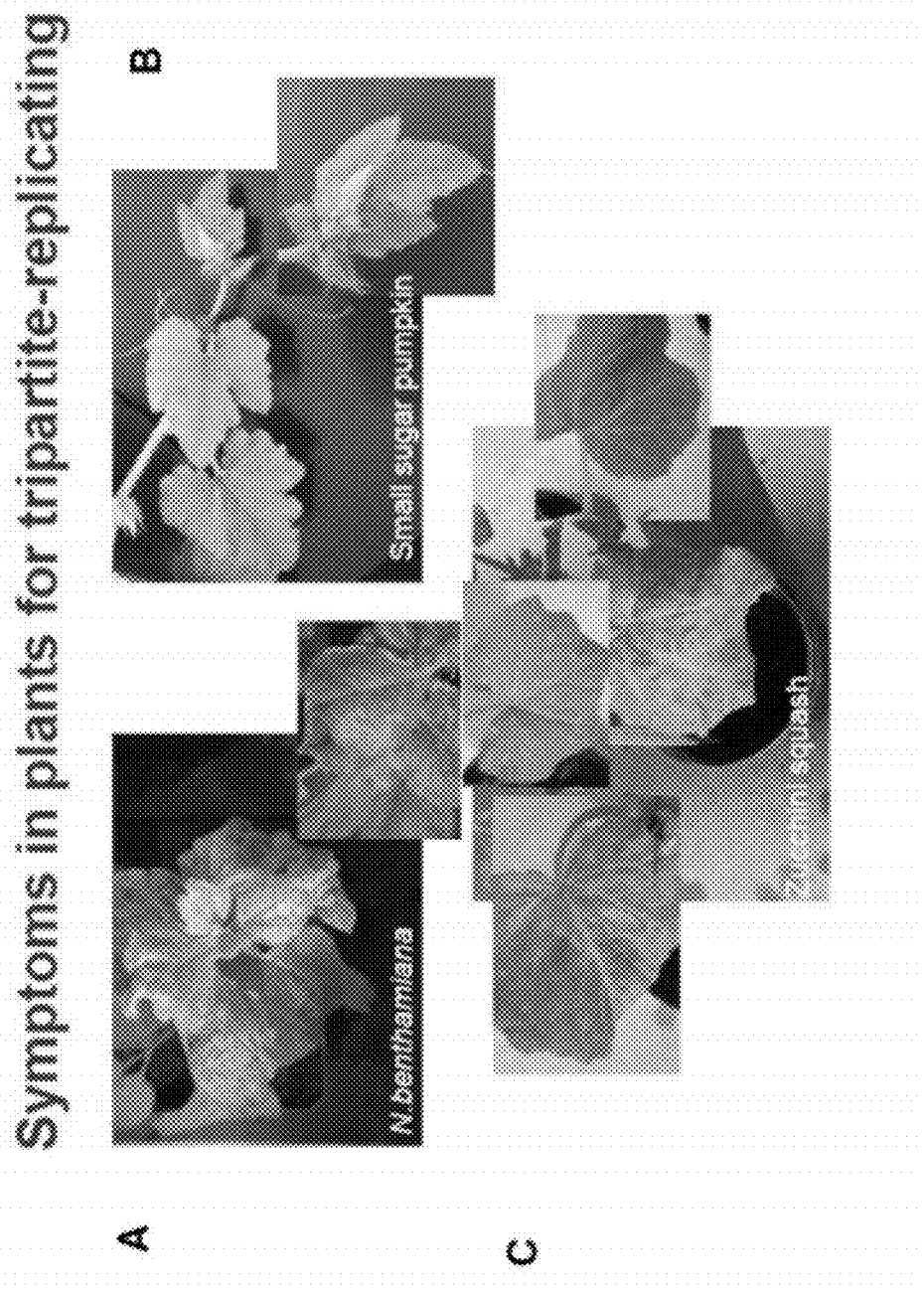
FIGS. 18A, 18B, and 18C depict symptoms in plants for tripartite-replicating. (A) depicts *N. benthamiana*; (B) depicts small sugar pumpkin; and (C) depicts Zucchini squash.
Figure 19:
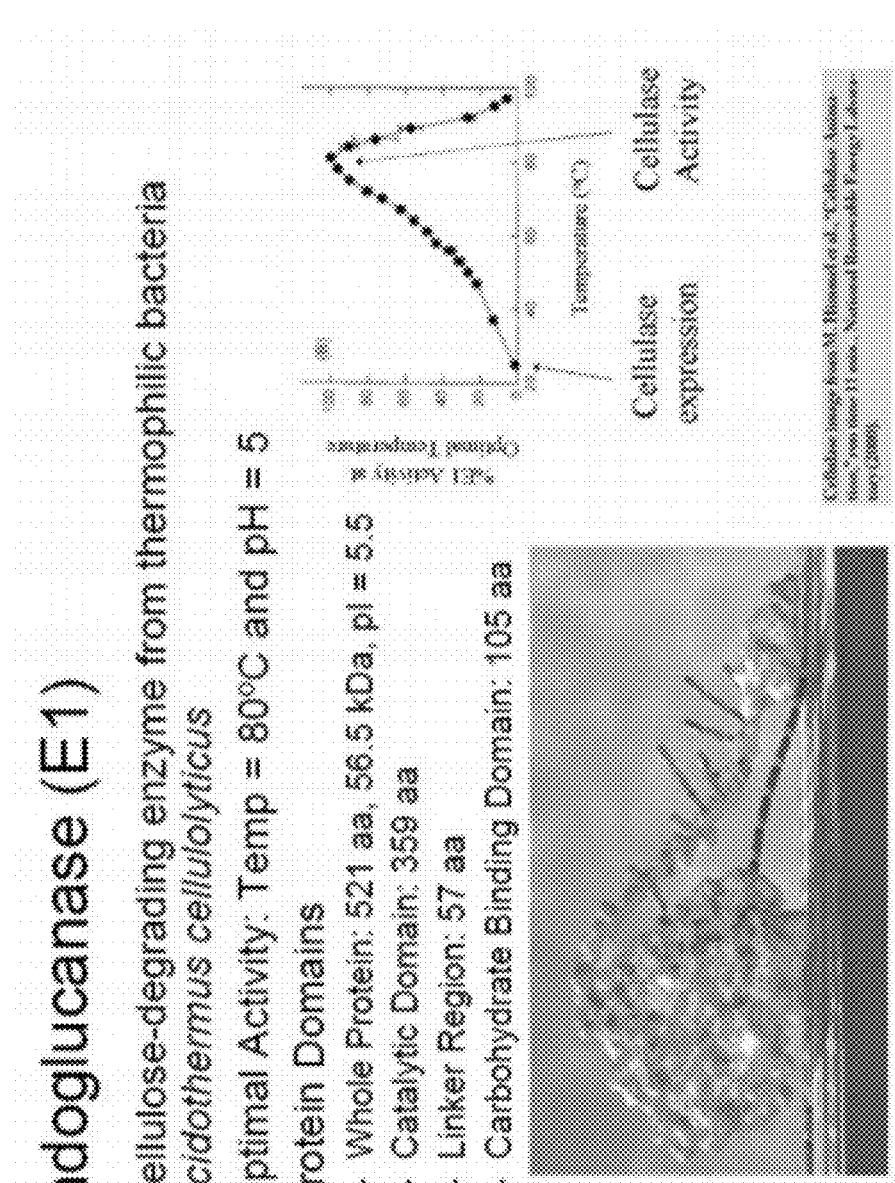
FIG. 19 depicts characteristics of *Acidothermus cellulolyticus* Endoglucanase (E1)
Figure 20:
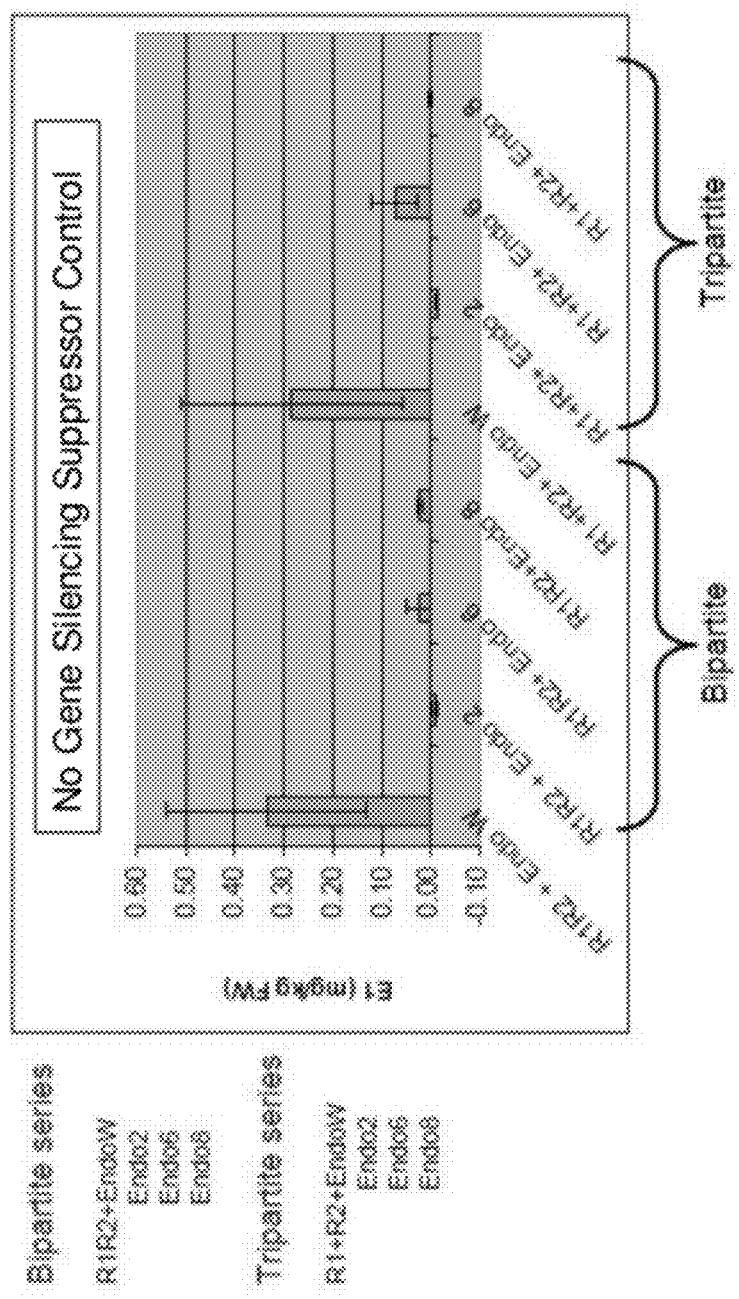
FIG. 20 depicts Endoglucanase (E1) expression controls (RT-PCR) using bipartite and tripartite vector systems in the absence of a gene silencing suppressor. Results for enzyme activity assays are shown (in mg/kg). W refers to wildtype, and 2, 6 and 8 refer to specific leader sequences. Results were obtained using non-transgenic *N. benthamiana* plants but with no co-expressed silencing suppressor protein.
Figure 21:
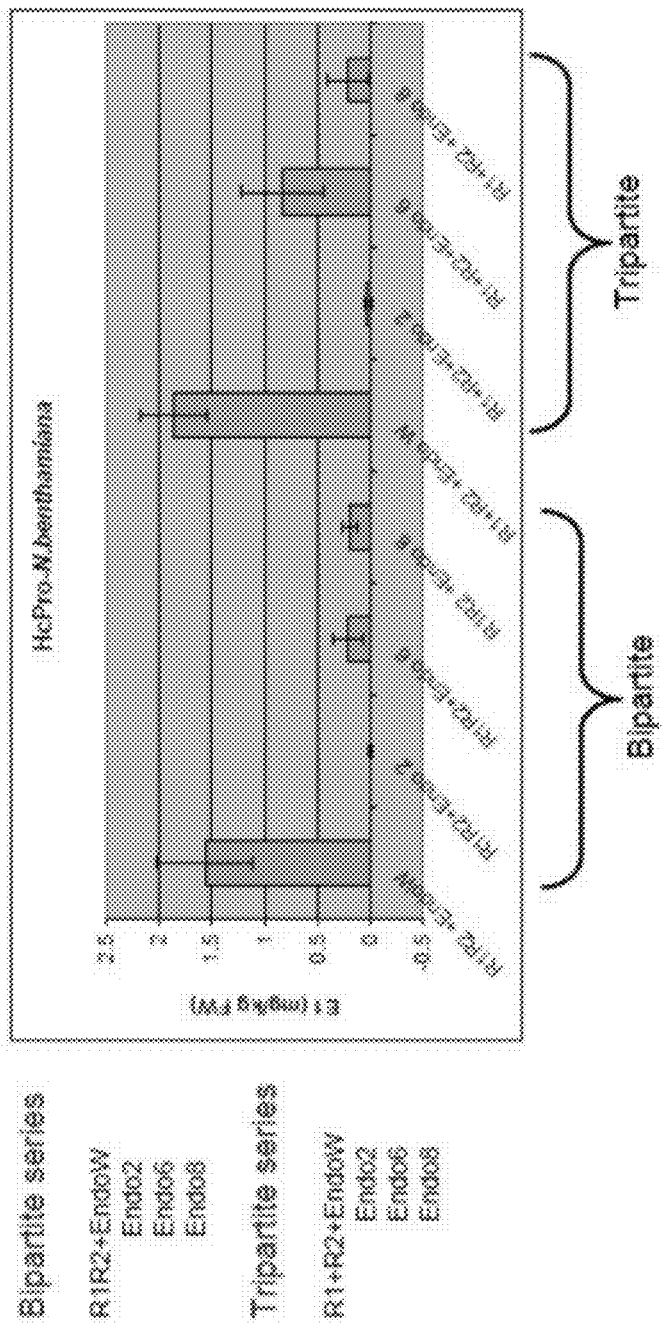
FIG. 21 depicts Endoglucanase (E1) expression using bipartite and tripartite vector systems in HcPro-*N. benthamiana* using RT-PCR. Results were obtained using the HC-Pro silencing suppressor expressed via transgenic *N. benthamiana* plants.
Figure 35:
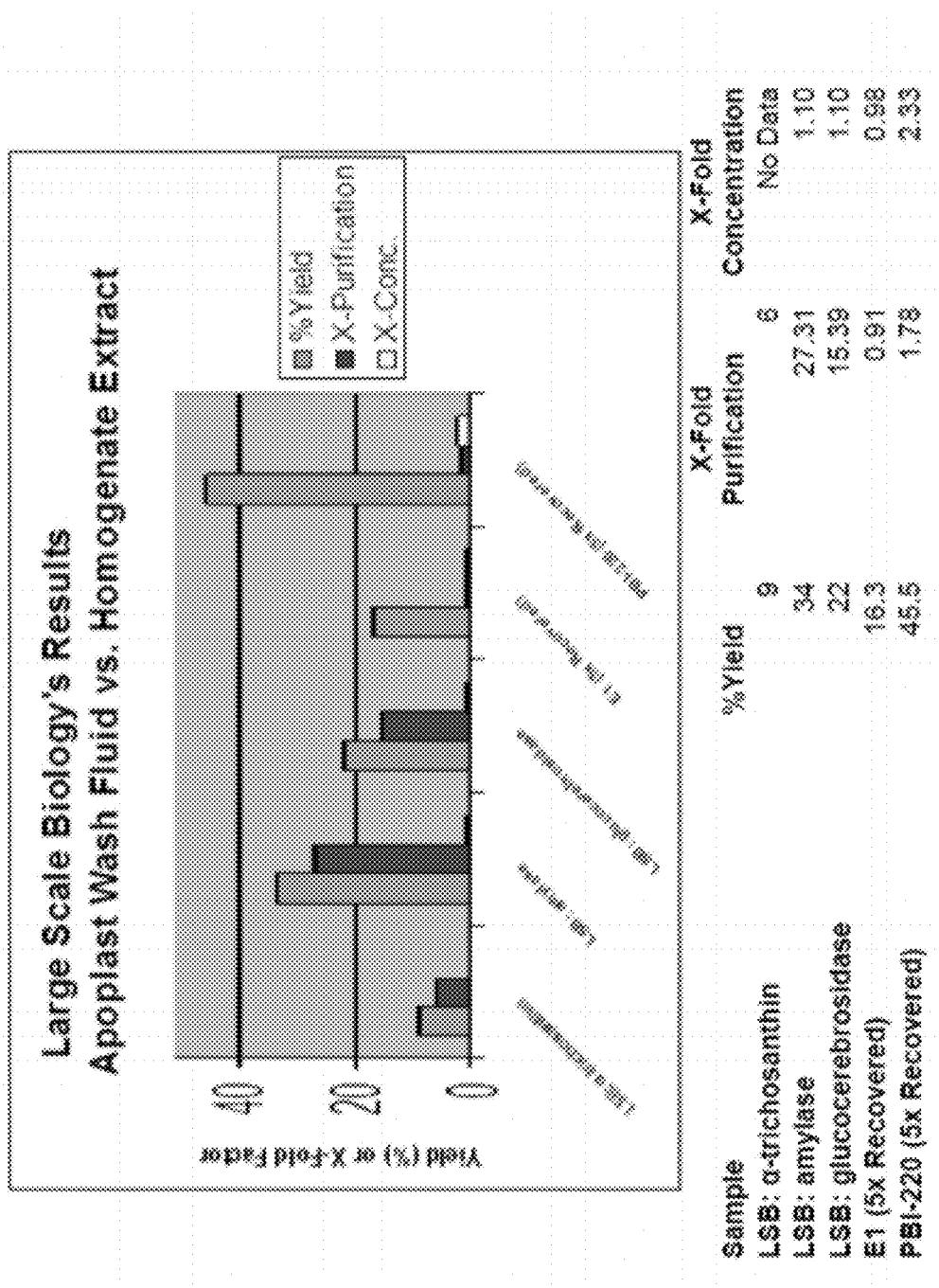
FIG. 35 depicts a comparison of the effectiveness of recombinant protein recovery by apoplast washing for five different proteins compared to what would be obtained through homogenate extraction. Large Scale Biology Corp. (LSB) results, as reported in U.S. Pat. No. 7,034,128, for three recombinant proteins grown in *N. tabacum* and recovered on a large scale appear next to the bench scale results obtained as part of an independent experimental series. Within this series, apoplast wash fluid (AWF) was collected five times per sample, as opposed to just one for the LSB data, and the data averaged or aggregated together. The data presented from the independent experimental series is representative of the best results achieved.

Alternatively, bipartite or tripartite expression systems may be used to encode viral amplicons, such as the CMV amplicon. In a bipartite system, amplicon segments such as CMV RNA 1, RNA 2, and RNA 3 are encoded on two different plasmids, in a tripartite system the segments may be encoded on three different plasmids (FIGS. 15 and 16). Amplicon segments in mono-, bi-, or tripartite expression systems may be modified. For example, amplicon segments may include promoter sequences that are responsive to chemical inducers, such as estradiol or methoxyfenozide. Amplicon segments, such as the CMV RNA 3 fragment RNA 4, may further include additional enzyme restriction sites in their leader sequences relative to the wild-type sequence (FIGS. 17 and 35). Amplicon segments, such as CMV RNA 3, may further be modified by replacing a viral nucleic acid sequence encoding a viral protein, such as the CMV coat protein, with a nucleic acid sequence containing a heterologous protein, Additionally, viral amplicon sequences may encode for virus protein mutants, such as mutants of the movement protein (MP). Specifically, a 33 amino acid deletion mutant of the CMV 3a movement protein was used to facilitate amplicon replication and systemic cell-to-cell movement of the viral amplicon in *N. benthamiana* plants and increased protein expression yields (FIG. 22).

Methods of Producing Heterologous Proteins Using Viral Amplicon-Based Expression Systems Generally, expression of heterologous proteins in plant cells using viral amplicon based expression systems includes the steps of i) contacting the plant cells with bacterial cells, such as *A. tumefaciens* cells, that contain an artificial viral amplicon; ii) allowing for a sufficient time, such as 2, 3, 4, 5, 6, 7, 8, 9, 10, 11, 12, 13, or 14 days, to produce the heterologous protein in a plant cell; and iii) harvesting the protein. Plant cells may be contacted with bacterial cells according to standard agroinfiltration protocols such as pressure infiltration or vacuum infiltration. Plant cells may be selected from plants including tobacco (e.g. *N. benthamiana*), switchgrass, miscanthus, sunflower, sugar pumpkin, or squash. The plant cells may be isolated cells that from part of a plant cell culture or they may form part of intact plants or excised plant tissues, such as plant leaves.

This disclosure describes several methods for increasing heterologous protein expression using viral amplicon-based expression systems. These methods may include suppressing heterologous gene silencing, facilitating amplicon replication and cell-to-cell movement, mechanical wounding of plant tissues, plant hormone treatments, and the optimization of leaf incubation temperatures (FIGS. 20-22, 25, and 29-37).

Figure 23:
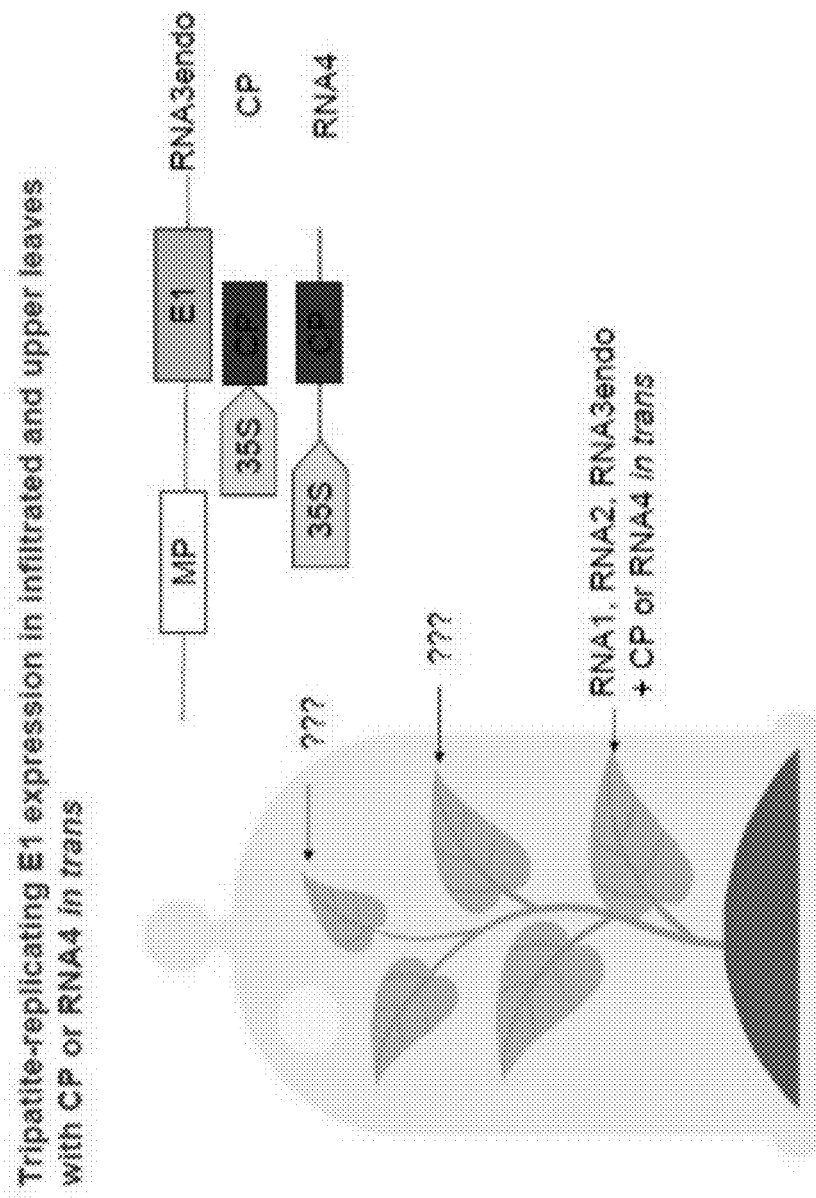
FIG. 23 diagrammatically depicts tripartite-replicating E1 expression in infiltrated and upper leaves with CP or RNA 4 in trans.
Figure 24:
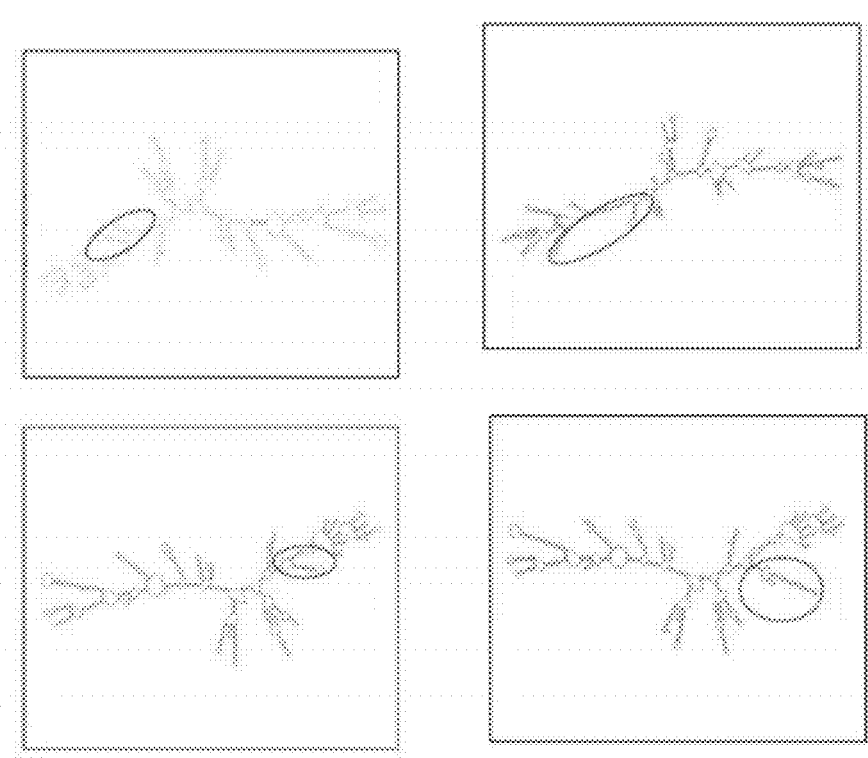
FIG. 24 depicts modified leader sequences (A) and their secondary structures (B). (A) Compared to the wild type RNA4 leader sequences, modified leader sequences contain additional sequences including additional enzyme restriction sites (wt (SEQ ID NO:2), 2+ (SEQ ID NO:3), 6+ (SEQ ID NO:4), 8+ (SEQ ID NO:5)). (B) Secondary structures of wild type and modified RNA 4 constructs are shown. Shared structural stem and loop elements are highlighted.
Figure 25:
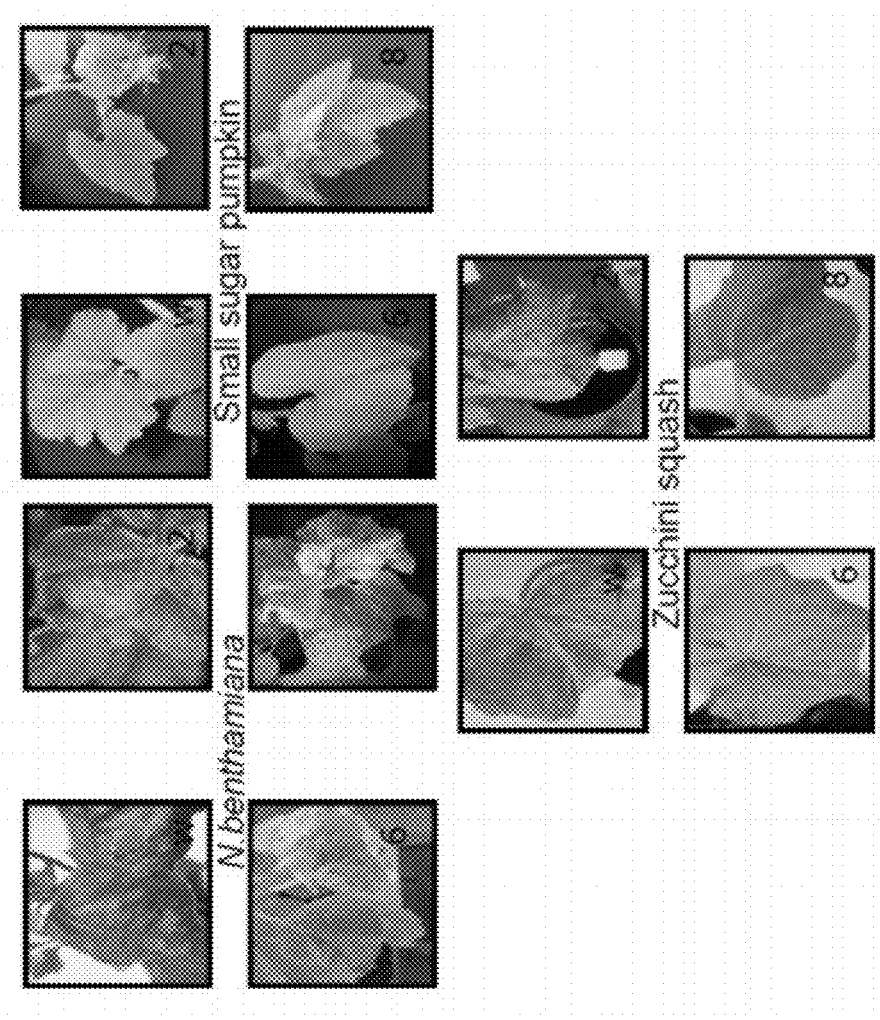
FIG. 25 depicts results for replicating tripartite amplicons infecting sugar pumpkin, squash and *N. benthamiana* plants. Plants were infected systemically and showed chloratic mosaic symptoms in upper systemic leaves 2 weeks after infiltration.
Figure 26:
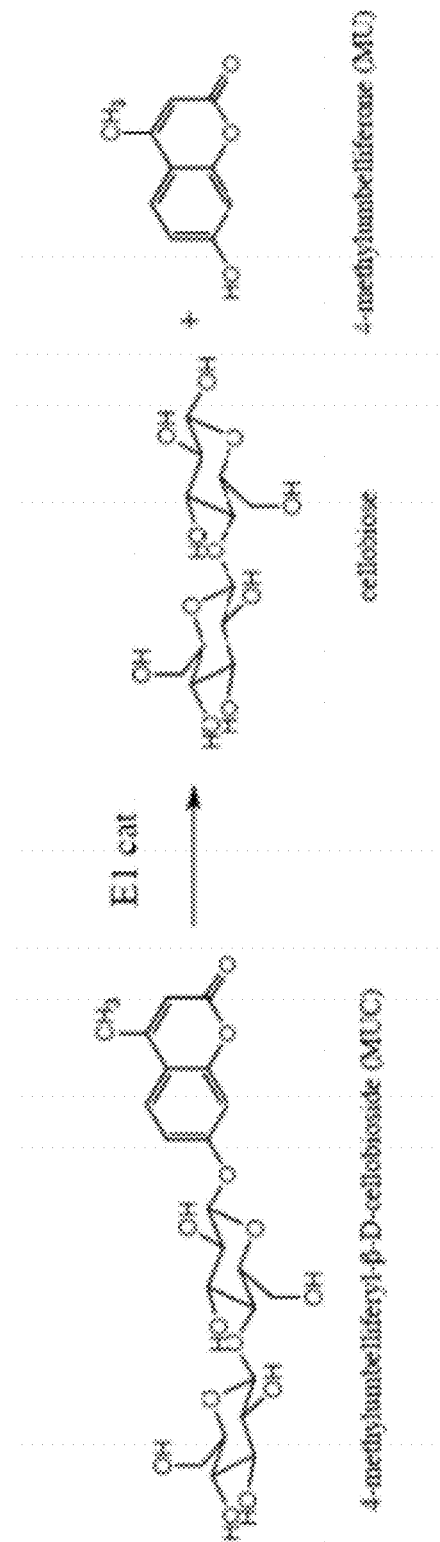
FIG. 26 depicts an E1 catalyzed reaction. The substrate MUC is cleaved into cellobiose and the fluorophore MU, the concentration of which can be monitored over time. When run at 65° C. and 135 µM MUC, this reaction is used as an E1 activity assay for plant extracts and yeast cultures.
Figure 27:
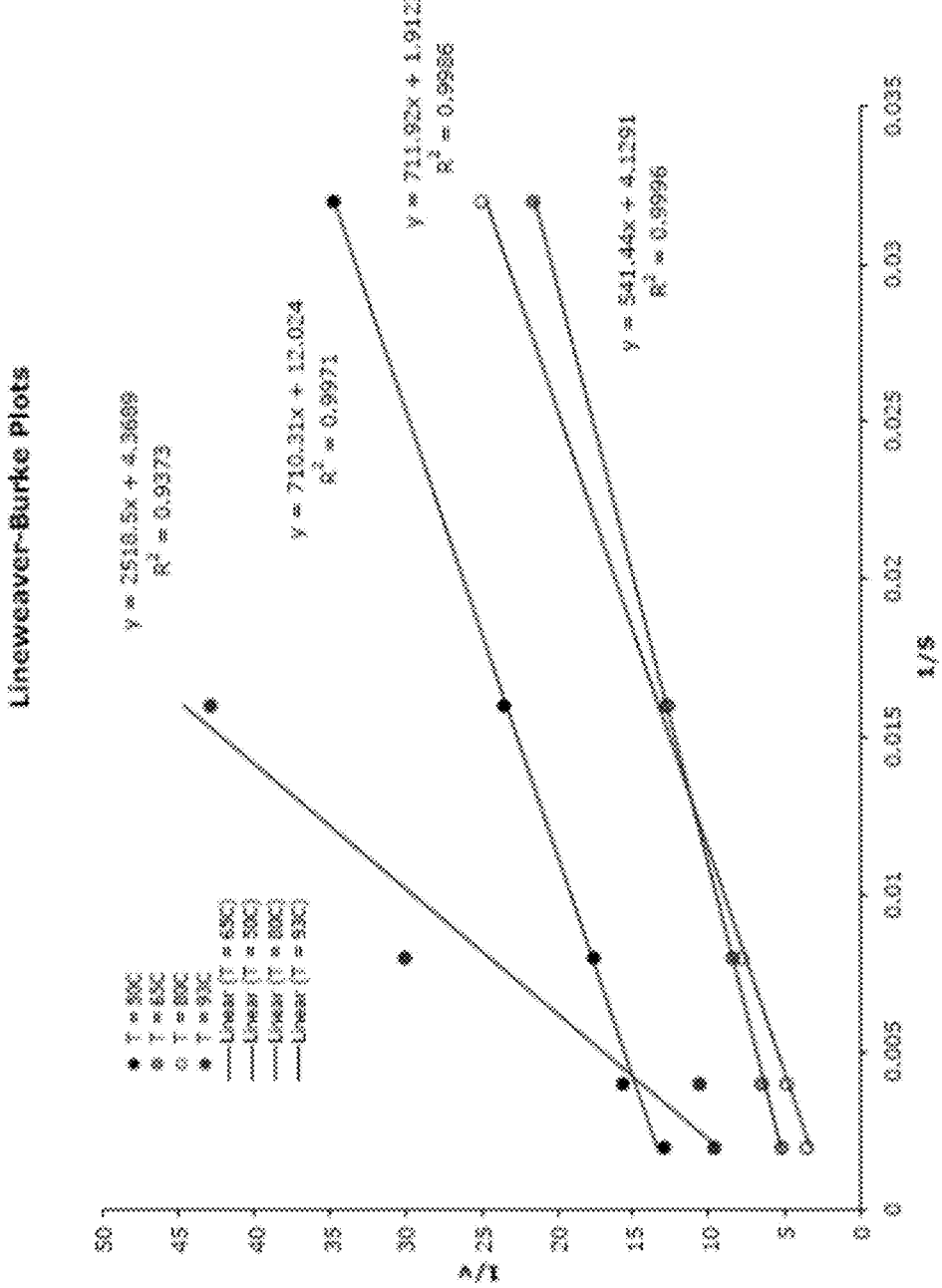
FIG. 27 depicts Lineweaver-Burke plots for E1 activity at different reaction temperatures (50, 65, 80, and 93° C.). Units of activity (V) are µM MU/min, and units of substrate concentration are µM MUC.
Figure 28:
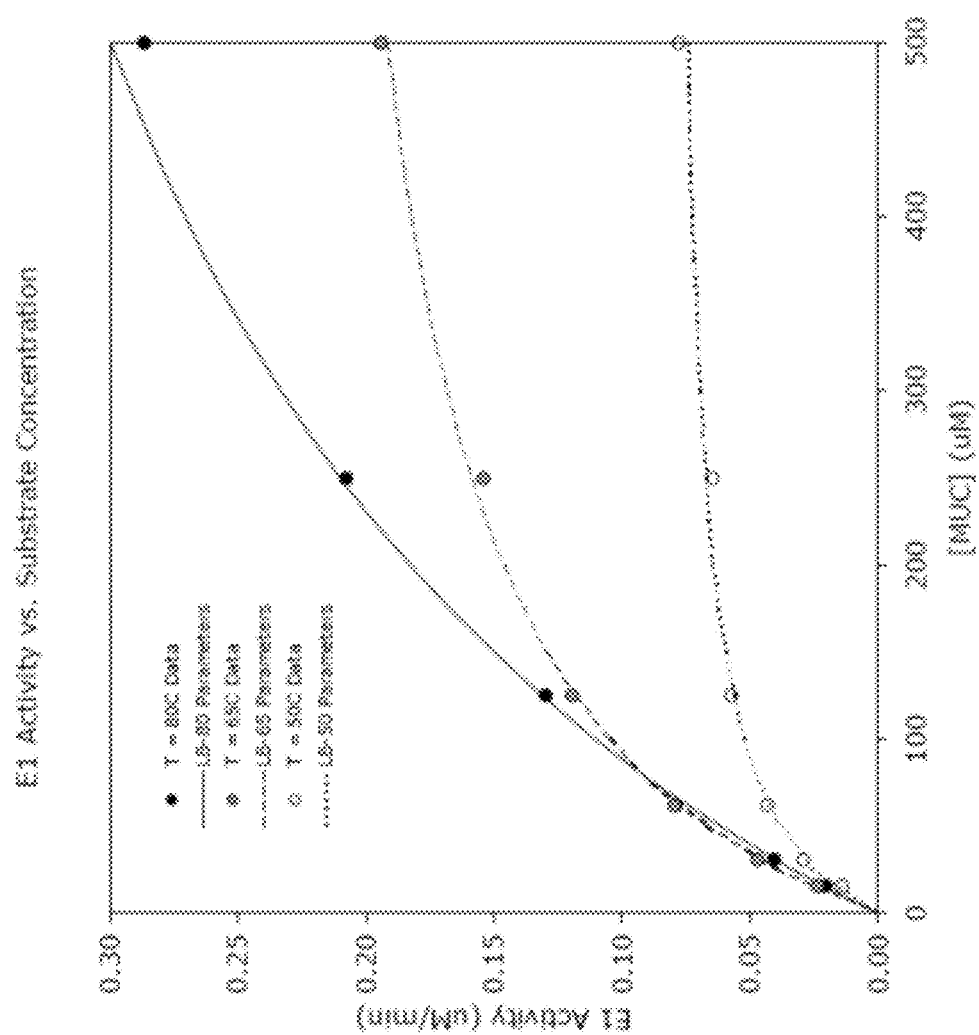
FIG. 28 depicts activity data plotted against substrate concentration. Lines represent Michaelis-Menten equation with experimentally-derived parameters.

For example, coexpression of the *A. cellulolyticus* endoglucanase E1 with the gene silencing suppressor HC-Pro was shown to significantly boost E1 expression in *N. benthamiana* cells (FIGS. 23 and 24). To enable cell-to-cell movement and systemic protein expression, CMV requires both the MP (3a movement protein) and the CP (capsid protein), both of which are encoded by RNA 3. When MP lacks the C-terminal 33 amino acids, CMV infections can move cell-to-cell in plants even without the CP. Therefore coexpressing a heterologous protein with a viral coat protein or movement protein deletion mutant may boost the expression of heterologous proteins by facilitating amplicon replication, cell-to-cell movement, and systemic expression of the heterologous protein (FIG. 22). Generally, coexpression of proteins such as HC-Pro, CP, or MP mutants with the heterologous protein may be achieved by agroinfiltration of plant cells producing the heterologous protein with bacteria cells containing plasmids encoding HC-Pro, CP, or MP mutant proteins. Alternatively, the plant cell producing the heterologous protein may be a transgenic plant cell that constitutively expresses HC-Pro, CP, or MP.

Figure 29:
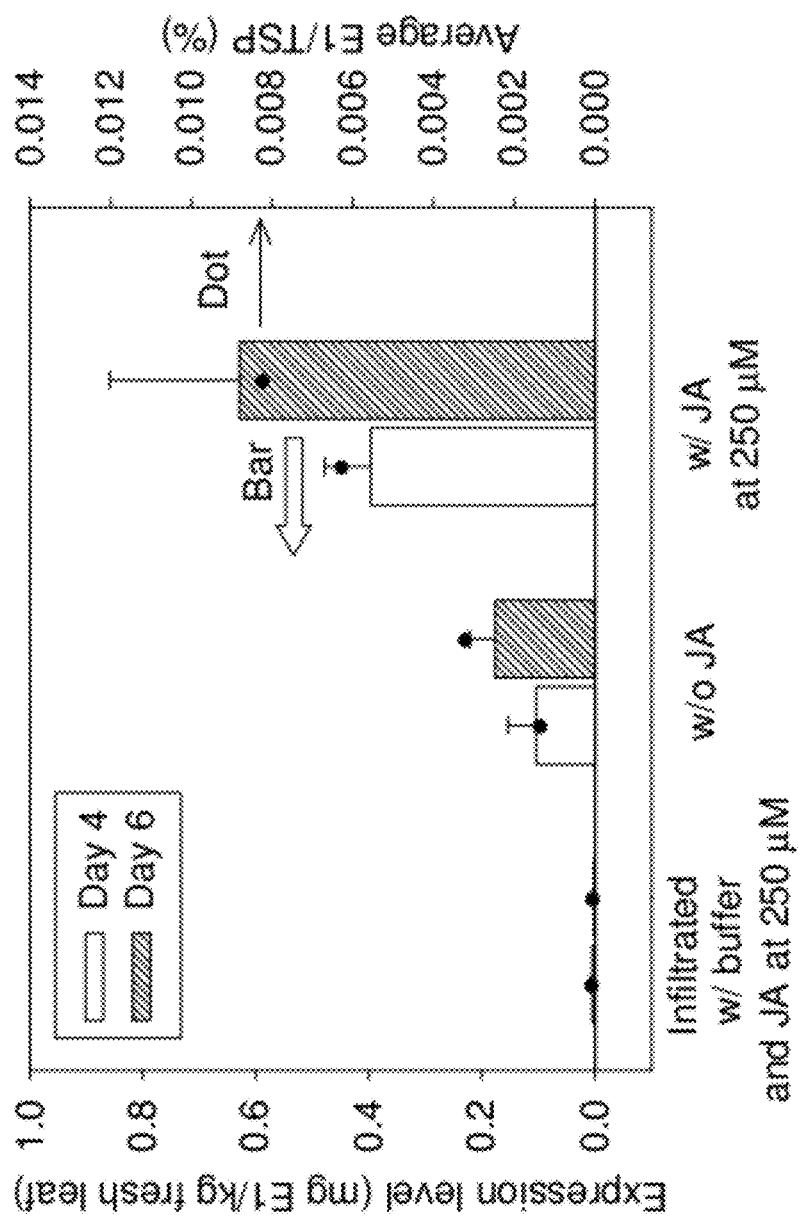
FIG. 29 depicts the effect of JA (jasmonic acid) on E1 expression. As shown in the figure, the addition of 250 µM of JA in the agroinfiltration solution increased expression level of E1 by 3.5 fold at Day 6 compared with the control leaves without JA.
Figure 30:
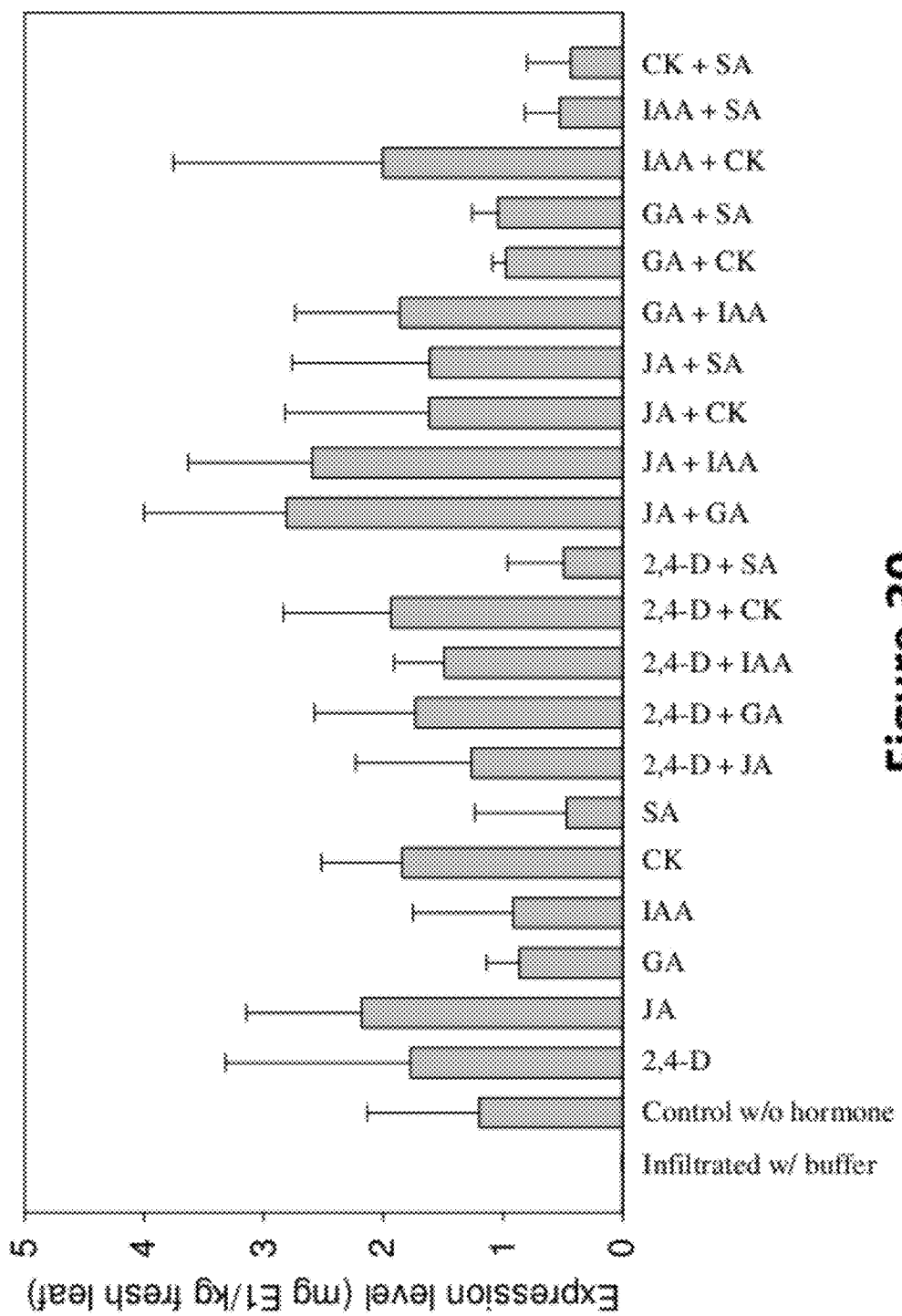
FIG. 30 depicts the effect of combinations of 2 different plant hormones, including jasmonic acid (JA), gibberellin A3 (GA), indole acetic acid (IAA), 2,4-dichlorophenoxyacetic acid (2,4-D), kinetin (CK), and salicylic acid (SA).

Mechanically wounding *N. benthamiana* tissue by pressing the tissue repeatedly with a brush right before agroinfiltration was shown to result in increased expression of the endoglucanase E1 (FIG. 29). Other experiments showed that treating plants or excised plant tissues with plant hormones right before agroinfiltration increased E1 expression (FIG. 30). Plant hormones such as jasmonic acid (JA), gibberellin A3 (GA), indole acetic acid (IAA), 2,4-dichlorophenoxyacetic acid (2,4-D), kinetin (CK), and salicylic acid (SA) may be applied individually or in combinations of at least two plant hormones (FIGS. 30-35).

Figure 31:
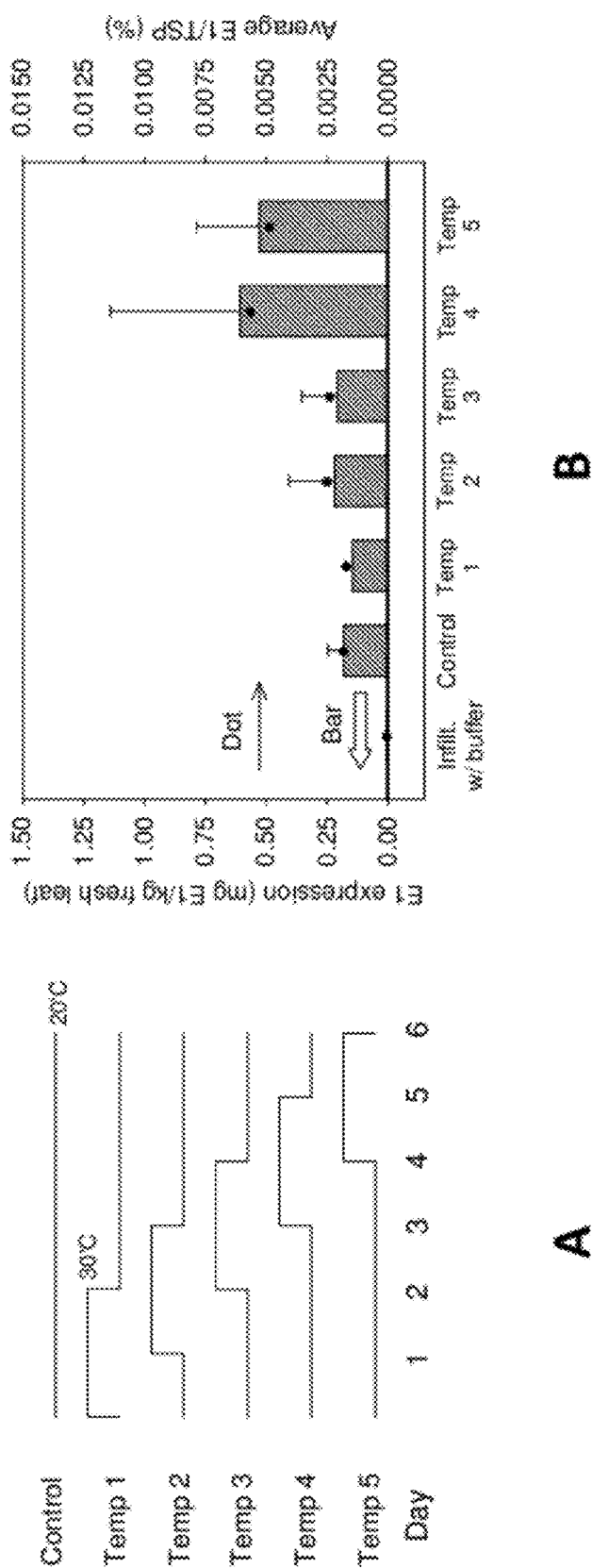
FIG. 31 depicts the effect of different temperature profiles during the leaf incubation. The leaf incubation temperature was shifted from 20 to 30° C. at different days following agroinfiltration and maintained for 2 days. Compared with the Control, Temp 4 or Temp 5 profile gave the highest expression. Increasing the incubation temperature in a late phase of incubation increases the production of E1.
Figure 32:
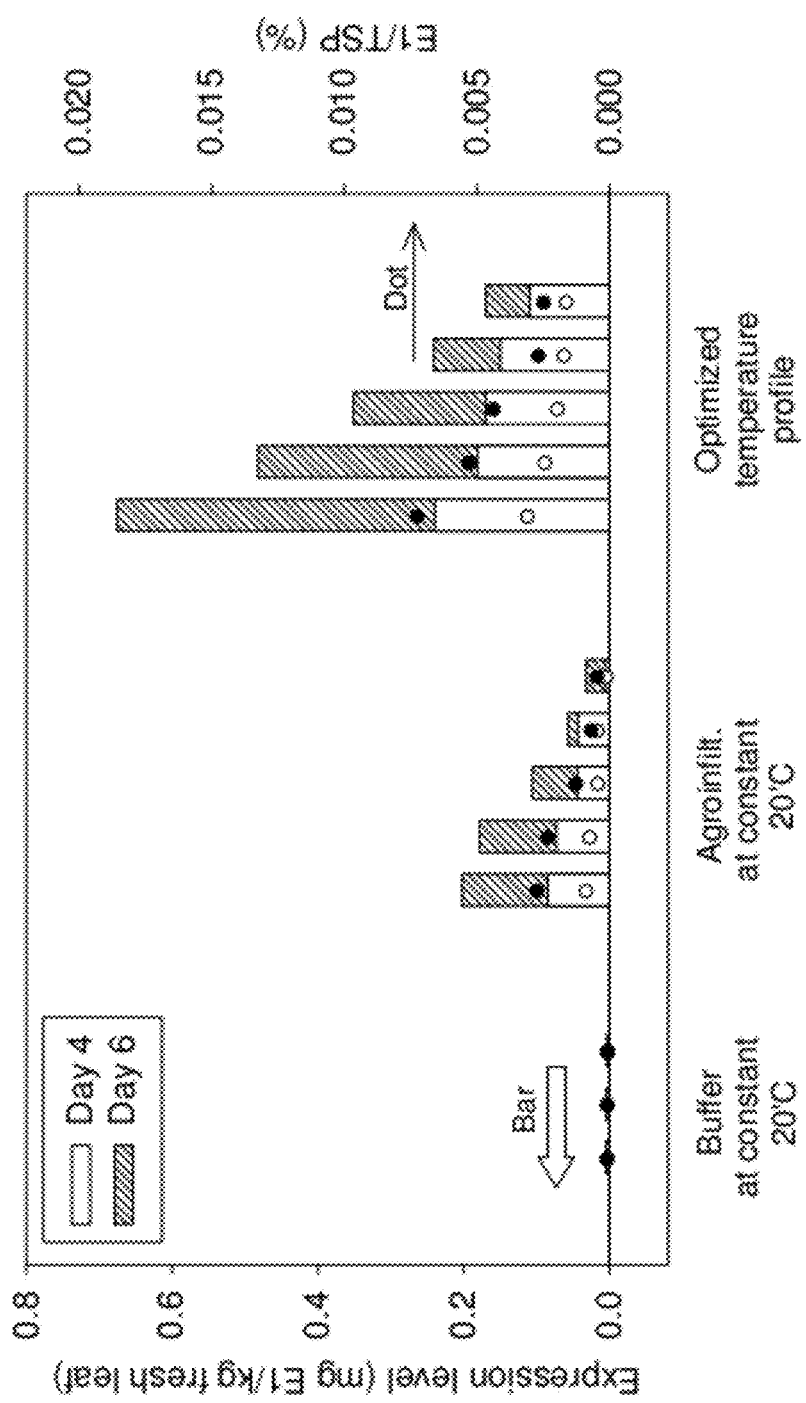
FIG. 32 depicts the two-phase optimization of leaf incubation temperature. Each bar represents an individual leaf. The incubation temperature was elevated at Day 2 from 20 to 26° C. and maintained at 26° C. for the following 4 days.
Figure 33:
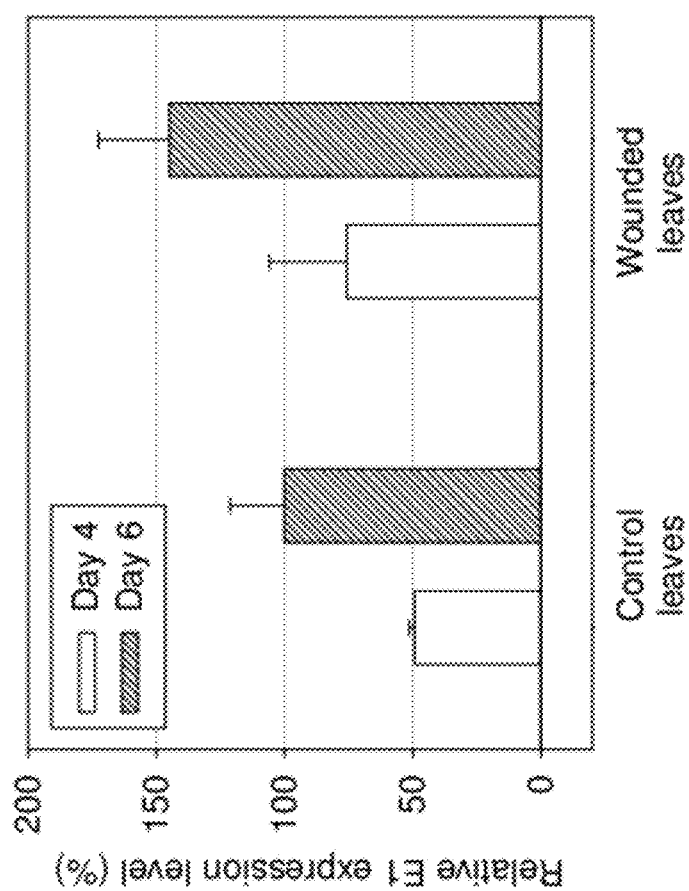
FIG. 33 depicts the effectiveness of mechanical wounding treatment on sunflower leaves. A plant leaf was pressed with a brush several times and then subjected to vacuum infiltration. The direct comparison between with and without the wounding treatment is illustrated.

Optimizing leaf incubation temperatures was shown to result in increased expression of E1 endoglucanase (FIGS. 31-32). The incubation period can be divided into an *Agrobacterium* infection phase and a protein production phase, and incubation temperatures can be optimized separately for both phases. The *Agrobacterium* infection phase may be a period of 1, 2, 3, 4, or 5 days after contacting the *Agrobacterium* with a leaf. The incubation temperature during the *Agrobacterium* infection phase may be 15, 16, 17, 18, 19, 20, 21, 22, 23, 24, or 25° C. The protein production phase may be a period of 1, 2, 3, 4, 5, 6, 7, 8, 9, 10, 11, 12, or 13 days following the *Agrobacterium* infection phase. The protein production temperature may be 26, 27, 28, 29, 30, 31, 32, 33, 34, or 35° C.

Generally, the CMV amplicon-based expression systems described herein were shown to generate protein yields of about 0.5, 1.0, 1.5, 2.0, 2.5, 3.0, 3.5, and 4.0 mg E1/kg fresh weight plant tissue (FIGS. 20-21 and 34-35).

As used herein, the term "about" refers to an approximation of a stated value within an acceptable range. Preferably, the range is +/−10% of the stated value.

FIGS. 14-39 disclose various viral amplicon systems, RNA species, and results described above. Figures illustrating results for the E1 construct show that the E1 construct containing the unmodified leader sequences gave consistent high expression levels, especially in the tripartite replicating system. This result may be due to CMV preferring its own wild type RNA3 recognized by the replicase complex. Additionally, recombined CMV amplicons containing subgroup I replicase complexes gave better E1 expression than the subgroup II replicase complex

EXAMPLES

The examples described below used the following materials and methods:

Materials and Methods

Plants and photography: Tobacco (*N. benthamiana*) seeds were germinated in compost and grown in a greenhouse. Three-week-old plants were used in the experiments. Plants were photographed with a Cannon G6 digital camera equipped with a Tiffen Deep Yellow 15 filter. Plants were illuminated with a hand-held long-wave UV lamp.

Infection of plant: The fully-developed cotyledons of 9-d-old squash (*Cucurbita pepo* L. cv. Green Bush), small sugar pumpkins, *N. benthamiana* were tested to see if it can move systemically. First, infected *N. benthamiana* leaf were grinded using motor and pestle in 50 mM $NaH_2PO_4$ (pH 7.0) and plants were mechanically inoculated by rubbing the upper surface of cotyledons gently in using silicon carbide powder (Carborandum grit 300, BDH, UK) as abrasive.

Agroinfiltration: Binary plasmids purified from *E. coli* cultures were transformed into *A. tumefaciens* strains GV3101 and EHA105 using an electroporator (BIO-RAD). Transformed cells were plated on Luria-Bertani plates containing Gentamycin (25 µg/ml), Kanamycin (50 µg/ml) and Rifampicin (10 µg/ml) when using GV3101, or Rifampicin (10 µg/ml), Gentamycin (20 µg/ml), and Tetracycline (10 µg/ml) when using EHA105, respectively. For agroinfiltration purposes, single colonies were inoculated in 5 mls L-MESA 10 medium (100 ml LB broth, 2 ml 0.5 M MES (pH 5.7), 20 µl 0.1M Acetosyringone) and grown to an OD600 of about 1.0. Cells were harvested by 10 minute centrifugation at 3,500×g and resuspended in agroinduction media (50 ml sterile $dH_2O$, 0.5 ml 1M $MgCl_2$, 1 ml 1 M MES (pH 5.7), 50 µl 0.1M acetosyringone), which was equilibrated at room temperature for over 3 hrs pre-infiltration. When mixed agrobacterial cultures were infiltrated into plants, bacterial cultures were prepared separately in induction media and combined immediately before infiltration.

Preparation of expression vector containing modified leader sequence for CP, E1 and GFP genes: An *agrobacterium*-based gene delivery system for the expression of the three CMV genome RNAs for replication and all four of the CMV-encoded proteins was developed. The pQA expression vector contains EcoRI-Pst I-Eco RI-HindIII restriction enzyme site. The leader sequence was modified by PCR primer tagging to include additional restriction sites and the expression system was inserted into the Sma I restriction site of the mini binary vector pCB301 (Xiang 1999) by blunt end ligation of pfu polymerase amplification products. The expression system includes a RK2 replication origin, the nptIII gene conferring kanamycin resistance in bacteria, and both the right and left T-DNA borders. All constructs were sequences-verified and tested in plant to express the coat protein by immunoblotting using specific antibodies. Expression clones 2, 6, 8 were selected based on their superior protein expression characteristics and a wild type leader sequence construct was chosen as a control. RNA3 expression constructs containing GFP and E1 instead of coat protein (CP) sequences were produced as follows. Briefly, the vector backbone was PCR amplified using primers designed to anneal to sequences just downstream of the CP ORF forward primer (5' end of the vector backbone) and to sequences just upstream of the CP ORF reverse primer (3' end of backbone) respectively. The vector backbone and pfu polymerase amplified GFP and E1 fragments were ligated by blunt end ligation. Subgroup I and II RNA1 and RNA2 constructs of the binary expression system were also produced by blunt end ligation of vector backbone and inserts. Vector backbones were prepared using 35ST forward and 35SP reverse primer sets. Subgroup I and II RNA1 and RNA2 were then pfu polymerase amplified and ligated. The sequences of all constructs were confirmed.

Secondary structure prediction: Secondary structures of RNAs were predicted using the mfold web-based program by Zuker (Zuker 2000).

RNA extraction and real-time RT-PCR: Samples for RNA and protein extraction were harvested from infiltrated leaves as well as non infiltrated leaves at 5 days after infiltration. RNA was extracted using RNeasy kits (Qiagen) according to the manufacturer's instruction and treated with RNase-free DNase I for 20 min at 37° C. After inactivating DNase 1,500 ng of total RNA were used for the reverse transcription with the random hexamer and superscript II reverse transcriptase, as described by the manufacturer's manual (Invitrogen). Real-time PCR was performed with gene specific primer sets for each RNAs using 7500 ABI program and analyzed. The 25 µl PCR included 5 µl RT product, 2×SYBR PCR Master Mix (Applied Biosystems), 400 nM gene-specific primers. Real-time PCR was performed in an ABI Prism 7500 Sequence Detection system (Applied Biosystems) under standard amplification conditions. Melting curve analyses was performed for each gene. Statistical analyses was carried out using the Tukey-Kramer test with P=0.05. The reactions were incubated in a 96-well plate at 95° C. for 5 min, followed by 40 cycles of 95° C. for 15 s and 60° C. for 1 min. All reactions were run in triplicate. The threshold cycle (CT) is defined as the fractional cycle number at which the fluorescence passes the fixed threshold.

Protein extraction and immunoblotting: Proteins were extracted from leaves into protein extraction buffer (100 mM Tris-HCl (pH 8.0), 10 mM EDTA, 5 mM DTT, 150 mM NaCl, 0.1% Triton X-100, 1× protease inhibitor (Roche)) by twice applying a bead-beater for 30 s. After removing all cell debris by centrifugation of the cell extracts at 12,000 rpm for 20 min, the protein concentrations of the supernatant were determined using a Bradford Protein Assay kit (BIO-RAD, USA) with bovine serum albumin as a standard. Proteins were extracted from leaves to and an SDS-PAGE analysis was performed (12% polyacrylamide gels). The fractionated proteins were transferred to a nitrocellulose membrane (Hybond-C; Amersham Pharmacia Biotech), incubated with rabbit anti-CP polyclonal antibody at 1:2500 dilution, followed by goat anti-rabbit IgG-alkaline phosphatase conjugate (1; 2500). After washing, purple substrate solution (BIO-RAD) was added and the reaction was quenched with distilled water.

Endoglucanase activity assay: Endoglucanase (E1) cleaves methylumbelliferyl-tagged cellobiose (MUC), releasing methylumbelliferone (MU). The MU fluorescence can be measured to determine E1 activity. The relative fluorescence readings of 0.024 to 3.0 µM MU solutions were used to create a linear standard curve. Samples containing E1 were diluted so the concentration of MU released fell within the standard curve. A 60 µl aliquot of diluted supernatant was added to 540 µl of acetate buffer (200 mM acetate, pH 5.5, 100 mM NaCl) and 200 µl of substrate (500 µM MUC). 200 µl of reaction was sampled at time zero and after 30 minutes and added to 800 µl of stop buffer (150 mM glycine, pH 10). The change in fluorescence over time was measured with a VersaFluor fluorometer (Bio-Rad). Fluorescence was converted to an activity, and the specific activity reported in the literature was used to approximate the concentration of E1 in *Pichia* supernatants.

Example 1

Bipartite and Tripartite Cucumber Mosaic Virus (CMV)-Based Expression Vectors for in Planta Protein Expression This example describes agroinfiltration-based methods for transient, high-yield production of heterologous proteins in plants. Heterologous protein expression is achieved through the use of a CMV amplicon-based expression system. The CMV amplicon is either encoded by two or three plasmids and contains amplicon segments from one or two viral subgroups.

Bipartite and Tripartite Systems Efficiently Express GFP, RFP and Coat Protein

First of all, bipartite and tripartite constructs were prepared to make a CMV-based heterologous protein expression system in plant. RFP and GFP expression was tested in bipartite and tripartite systems to confirm that the tripartite system can be used to produce a variety of heterologous proteins in plant. All three genome segments including 35S promoter and terminator sequences were amplified and ligated to pCB301 using blunt-end ligation and sequences were confirmed. For the bipartite system, RNA3-containing binary vector and pDU97XLR1R2 were mixed together and the mix was used to infiltrate *N. benthamiana*.

For GFP expression, the coat protein region was removed from RNA3 using a forward primer starting exactly downstream of ORF and a reverse primer stating exactly before the ORF. GFP sequences were amplified using specific primers and ligated to the RNA3 vector product. For RFP, the same cloning method was used. *Agrobacteria* were transfected with a mix containing all three RNA 1, RNA 2, RNA 3 constructs. In the case of the bipartite expression system estradiol was applied with a cotton applicator 16 hours post-infiltration. Five days post-infiltration, the infiltrated leaves were harvested and the total protein extracted. In the case of both GFP and RFP, both bipartite and tripartite systems worked well. RFP expressed very well in planta as indicated by the red color visualized microscopically using RFP filter settings. GFP expression was detected under UV light. The tripartite system showed similar, if not higher, protein expression compared to the bipartite system. All leaf tissues were analyzed 5 days post-infiltration.

Modified Leader Sequences of RNA4 Increase Coat Protein Expression Levels and RNA Levels To simplify cloning of the amplicon, the three CMV amplicon segments RNA1, RNA2, and RNA3 were separated into different plasmids and several additional restriction sequences were introduced in the region upstream of the coat protein (i.e. the coat protein gene to be replaced by other genes of interest) and downstream of the leader sequences (FIG. 24). Then, several constructs were prepared containing different leader sequences of RNA 4 for coat protein expression. FIG. 24 shows several leader sequences of the constructs, including wild type leader sequences. Compared to wild type leader sequences, modified sequences have additional sequences containing restriction enzyme sites (FIG. 24A, italicized and underlined) that facilitate the insertion of heterologous genes into the region downstream of the RNA4 subgenomic promoter. According to the RNAfold computer program, modified leader sequences still contain secondary stem and loop structures (FIG. 24B).

These constructs were then used for agroinfiltration. Protein expression was tested in several different plants, including tobacco (*N. benthamiana*), small sugar pumpkin and zucchini squash. Pumpkin is known to be sensitive to CMV infection. Because the plant is nutrient rich it is expected to support high-level protein expression. To this end, pumpkin cotyledon was inoculated with the sap of infiltrated leaves and frequently checked for symptoms of CMV infection such as spot formation on leaves. When using the tripartite expression system (containing all three amplicon segments RNA 1, RNA2, and RNA3) characteristic symptoms could be observed on the systemic leaves seven days after inoculation (FIG. 25). Contrary to the tripartite system, the bipartite system containing the deleted 5' 46 bp of RNA1 could not move systemically in pumpkins or cause the symptomatic spot formation on pumpkin leaves. These results demonstrate that the tripartite system can replicate in planta and move systemically in its host and spread. These are important advantages of the tripartite system over any other system, including the CMViva monopartite system. The biggest advantage of the CMViva monopartite system is that all three RNA components are encoded by the same plasmid and following agroinfection will be located and expressed in the same cell. However, the CMViva monopartite system contains a RNA1 deletion, virus particles cannot replicate and protein expression is dependent on estradiol induction. In summary, the disclosed tripartite system efficiently expresses heterologous proteins in plant, including CMV coat protein, GFP and RFP. Furthermore, the tripartite system moves systemically in pumpkin.

qPCR and immunoblot analyses demonstrated that RNA4 constructs containing modified leader sequences express higher levels of coat protein than wild type RNA4. Expression profiles were similar in the bipartite or tripartite expression systems. Monopartite systems, including CMViva and Q123, produced slightly more coat protein in plant than bipartite or tripartite systems. To determine the effects of the leader sequences on the RNA level, real-time RT-PCR was performed to quantify RNA levels in infiltrated plants. Using the relative Ct values to healthy control, RNA1, RNA2, RNA3, and RNA3 including RNA4 levels were estimated relative to the wild type RNA4 leader sequence construct. In the bipartite system, higher RNA3 and RNA4 levels were found for constructs containing modified leader sequences than for the corresponding wild type construct, thereby explaining higher protein expression. Interestingly, with respect to relative levels of RNA 1 and RNA2 expression, experiments containing all three components RNA 1, RNA2, and RNA3 yielded higher RNA levels than experiments where RNA3 was absent. This trend was especially pronounced in the tripartite system. RNA3 expression levels were higher than RNA1 or RNA2 expression levels regardless of whether mutant or wild type leader sequences were used. In the tripartite system, wild-type constructs containing all three RNAs yielded higher coat protein RNA levels compared to the coat protein RNA levels yielded by RNA constructs including modified leader sequences. This result was mirrored at the level of protein expression.

To assess the expression of proteins other than coat protein GFP clones were prepared containing the same leader sequences as previously used for coat protein expression. Using the same methods described as before plants were infiltrated with the GFP constructs and fluorescence was detected under UV light 6 and 10 days after infiltration. GFP expression driven by modified leader sequences yielded slightly brighter fluorescence intensities than wild type leader constructs. In comparison, the tripartite system expressed GFP at similar or even slightly higher levels as the bipartite system.

In Planta Endoglucanase (E1) Expression Using Bipartite and Tripartite Expression Systems Next the described protein expression systems were used to produce endoglucanase E1, a cellulose-degrading enzyme. The particular endoglucanase chosen is naturally produced by the thermophilic bacteria *A. cellulolyticus*. This bacterium is found, for example, in the hot springs of Yellowstone National Park. The bacterial enzymes are most active at high temperatures and low pH. The mature protein contains 521 amino acids, has a molecular weight of 56.5, and an isoelectric point of 5.5. The first 359 amino acids form the catalytic domain. There is a linker region of about 57 amino acids that connect the catalytic domain to the carbohydrate binding domain, which itself spans the C-terminal 105 amino acids. Because endoglucanase attaches to plant tissues via its carbohydrate domain, it could not be fully recovered from cell debris during protein extraction and purification.

E1 endoglucanase was expressed in both the bipartite and tripartite protein expression system. In both cases bipartite and tripartite expression constructs were co-infiltrated with silencing suppressor HC-Pro. Generally, in both the bipartite and tripartite expression systems, modified leader sequences of E1 constructs increase the yield in terms of enzymatic activity (FIGS. 20-21)

Enhancing CMVva Replication Capabilities

CMV has very broad host range; it infects more than 1,000 plants and CMV isolates have been recovered from throughout the world. CMV strains are divided into two subgroups, I and II. The previously described CMV expression systems were based on subgroup II strains. Subgroup I strains are more common and typically show more severe symptoms than do subgroup II strains, perhaps due to a higher level of viral replication. In addition, subgroup I strains encode for a stronger version of the 2b silencing suppressor protein as compared to subgroup II. Because of these traits, a subgroup I CMVva tripartite system was developed. First it was tested whether the subgroup I RNA1 and RNA2 facilitate expression of the subgroup II RNA3 developed previously. GFP expression was assessed and much higher GFP expression was visualized using subgroup I vs. subgroup II replicase components. Next endoglucanase expression was tested and much higher protein expression was found with the subgroup I replicase than with the subgroup II replicase system.

Exemplary results for viral bipartite and tripartite amplicon systems using rearranged subgroup I and II segments are shown in FIGS. 20 and 21. In a typical experiment, rearranged viral amplicon systems encoding subgroup I replicases yielded higher protein expression and enzyme activity levels than viral amplicon systems encoding subgroup II replicases. CMVva with Cell-to-Cell Movement Capabilities For cell-to-cell movement, CMV requires both the MP (3a movement protein) and the CP (capsid protein), both of which are encoded by RNA 3. When MP lacks the C-terminal 33 amino acids, CMV infections can move cell-to-cell in plants even without the CP. The previously described CMVa expression system lacks cell-to-cell movement (due to the substitution of the CP gene with a product gene of interest), thus desired proteins are expressed only in the initially-infected cells. To reestablish cell-to-cell movement capabilities, a 33 aa deletion MP mutant was generated that also expressed endoglucanase via the CP coding region. When these constructs were infiltrated using the tripartite CMVva expression system, higher levels of endoglucanase expression were achieved, as determined both by immunoblotting and enzymatic activity assay.

Next, the 33 amino acid MP deletion mutant was tested for its ability to promote additional yield increases in in planta protein expression. The GFP construct containing a wild type leader sequence produced strong fluorescence signals under UV light when expressed in the presence of a subgroup I replicase. Construct #6 containing a modified leader sequence yielded much higher levels of GFP expression in the presence of a subgroup I replicase when combined with the MP deletion mutant than in combination with wild type MP. Use of subgroup I replicase and the MP deletion mutant also strongly increased in plant expression of E1 as determined by enzyme activity measurements. The highest E1 activity levels were achieved in planta when using a subgroup I replicase complex 26 in combination with the 33 amino acid MP deletion mutant. Wild-type MP was found not to express well when used in combination with subgroup I replicases. The MP deletion mutant, on the contrary, was found to express well in combination with subgroup I or II replicases.

In conclusion, this example demonstrates that CMV amplicon-based protein expression systems can efficiently produce a variety of heterologous proteins, including the *A. cellulolyticus* endoglucanase E1. The CMV amplicon can be divided into bipartite or tripartite expression systems in which CMV amplicon segments RNA 1, RNA 2, and RNA3 are distributed over two or three different plasmids. Combining CMV subgroup I segments RNA 1 and RNA 2 with CMV subgroup segment RNA 3 results in increased yields in protein expression. In some instances the optimization of RNA 4 leader sequences resulted in improved protein and RNA expression levels. Importantly, the expression of CMV 3a movement protein deletion mutants facilitated replication and cell-to-cell movement of the CMV amplicon and systemic expression of heterologous proteins such as GFP or E1. CMV amplicon-based expression systems were shown to generate yields of heterologous proteins of up to about 4 mg protein/kg fresh weight plant tissue.

Example 2

Production and Characterization of Endoglucanase (E1) Protein in *Pichia pastoris* for Use as a Standard This example demonstrates that *P. pastoris*-produced E1 can be used as a standard for the assessment of specific activities and yields of plant-produced E1.

The Michaelis-Menten kinetic parameters of purified endoglucanase were determined. The E1 was produced in *P. pastoris* and purified by IMAC (immobilized metal affinity chromatography). The parameters were determined for the specific reaction shown in FIG. 26. E1 cleaves the substrate (MUC) into cellobiose and a fluorophore (MU), the concentration of which can be monitored over time. When run at 65° C. and 135 μM substrate, this is the reaction used for the activity assay for E1 in plant extracts and yeast cultures. In this set of experiments, the substrate concentration was varied to determine the kinetic parameters at different temperatures.

The rate for a reaction displaying Michaelis-Menten kinetics is shown in Equation 1. The rate depends on the catalysis rate (kcat), the total enzyme concentration (ET), the adsorption/desorption rates which are lumped into the Michaelis-Menten constant ($K_M$), and the substrate concentration (S). At high substrate concentrations ($S \gg K_M$), the rate approaches a maximum, and kcatET is often written as $V_{max}$.

$$V = \frac{k_{cat} \cdot E_T \cdot S}{K_M + S} \quad \text{Equation 1}$$

$$V_{max} = k_{cat} \cdot E_T$$

$$\frac{1}{V} = \frac{K_M}{V_{max}} \cdot \frac{1}{S} + \frac{1}{V_{max}} \quad \text{Equation 2}$$

The parameters $V_{max}$ and $K_M$ can be determined experimentally by varying the substrate concentration (S) and measuring the reaction rate (V) at each concentration. Equation 1 can be rearranged as a linear equation (Equation 2). When the reciprocal of the reaction rate (V) is plotted against the reciprocal of the substrate concentration (S), a line fitting the data points can be used to determine $K_M/V_{max}$ (the slope) and $1/V_{max}$ (y-intercept). This type of plot is called a Lineweaver-Burk plot and the plots at different temperatures are shown in FIG. 27. The kinetic parameters calculated from the fitted line equations are summarized in Table 1. A Bradford assay was used to determine the E1 protein concentration in each sample, and this value of ET was used to calculate the kcat values in Table 1.

Table 1 depicts a summary of Michaelis-Menten parameters for E1-catalyzed degradation of MUC to MU at various temperatures. Values determined from fitted lines shown in FIG. 27.

TABLE 1

Summary of E1 Enzyme Activity Data

| Temp (° C.) | $V_{max}$ (uM/min) | $K_M$ (uM) | $k_{cat}$ (l/min) |
|---|---|---|---|
| 50 | 0.083 ± 0.003 | 59 ± 3 | 106 ± 5 |
| 65 | 0.242 ± 0.006 | 131 ± 4 | 309 ± 13 |
| 80 | 0.523 ± 0.070 | 372 ± 50 | 667 ± 92 |
| 93 | 0.229 ± 0.222 | 576 ± 570 | 292 ± 284 |

Because the uncertainty associated with the parameters at 93° C. approach 100% of the parameter values, the data at 93° C. were not used any further. The remaining parameters were plugged into the Michaelis-Menten equation and the equations were plotted with the original data, as shown in FIG. 28.

The kinetic parameters determined from the linear plots generate a good model for the experimental data. From the literature, plant-derived E1 has maximum activity at 81° C. In this set of experiments, the highest value of kcat (and therefore $V_{max}$) was achieved at 80° C. This value can be determined more accurately with additional experiments at temperatures close to 80° C. These data further support the idea that the *P. pastoris*-produced E1 is a suitable standard protein to use in assays for plant-produced E1.

Example 3

Expression of Endonuclease (E1) in Harvested Sunflower Leaves

This example explores strategies for the improvement of protein expression methods using *Agrobacterium* mediated transient expression systems.

Coinfiltration of with plant hormones. Plant hormones are small molecules that are essential for plant development, differentiation, immune response, or stress response. One interesting fact is that *Agrobacteria* is known to have genes for the synthesis of plant hormones and alters the hormone balance in plant cells. For this example, a plant hormone was added directly to the *Agrobacterium* suspension medium and then vacuum infiltrated into plant leaves. FIG. 29 shows the effect of JA (jasmonic acid). As shown in the figure, the addition of 250 µM of JA in the agroinfiltration solution increased expression level of E1 by 3.5 fold at Day 6 compared with the control leaves without JA. Next, the effect of combinations of multiple plant hormones was tested, including jasmonic acid (JA), gibberellin A3 (GA), indole acetic acid (IAA), 2,4-dichlorophenoxyacetic acid (2,4-D), kinetin (CK), and salicylic acid (SA). FIG. 30 shows the effect of combinations of 2 different plant hormones. From the result, synergistic (positive) or negative effects between hormones were identified. For example, when both JA and GA were infiltrated into plant leaves, it gave the highest E1 expression whereas SA likely inhibited E1 expression.

Optimization of leaf incubation temperature. The optimal temperature for *Agrobacterium* T-DNA transfer is known to be about 19~22° C. from early studies on the development of tumors on plants or mating experiments of bacteria. At temperatures higher than 29° C., many researchers failed to produce tumors or observe successful mating or T-DNA transfer (Fullner & Nester, J Bacteriol, 1996, 1498-1504). It also has been demonstrated that certain vir proteins are unstable at high temperature (Chen, Li, & Nester, PNAS, 2000, 13: 7545-7550). In contrast, biosynthesis rates in plant cells is maximized at higher temperatures such as 25-35° C. Thus, it implies that two different processes (T-DNA transfer and protein production) have different optimal temperatures. Therefore the incubation period was divided into an *Agrobacterium* infection phase and a production phase, and optimized incubation temperature for both phases. FIG. 31 shows the effect of different temperature profiles during the leaf incubation. The leaf incubation temperature was shifted from 20 to 30° C. at different days following agroinfiltration and maintained for 2 days. Compared with the Control, Temp 4 or Temp 5 profile gave the highest expression. Increasing the incubation temperature in a late phase of incubation increases the production of E1. Based on the result, two phase optimization of leaf incubation temperature was demonstrated as shown in FIG. 35 (each bar represents an individual leaf). For the data shown in FIG. 35 the incubation temperature was elevated at Day 2 from 20 to 26° C. and maintained at 26° C. for the following 4 days. Overall, the average E1 expression was increased 3.3 fold compared with the control.

Figure 36:
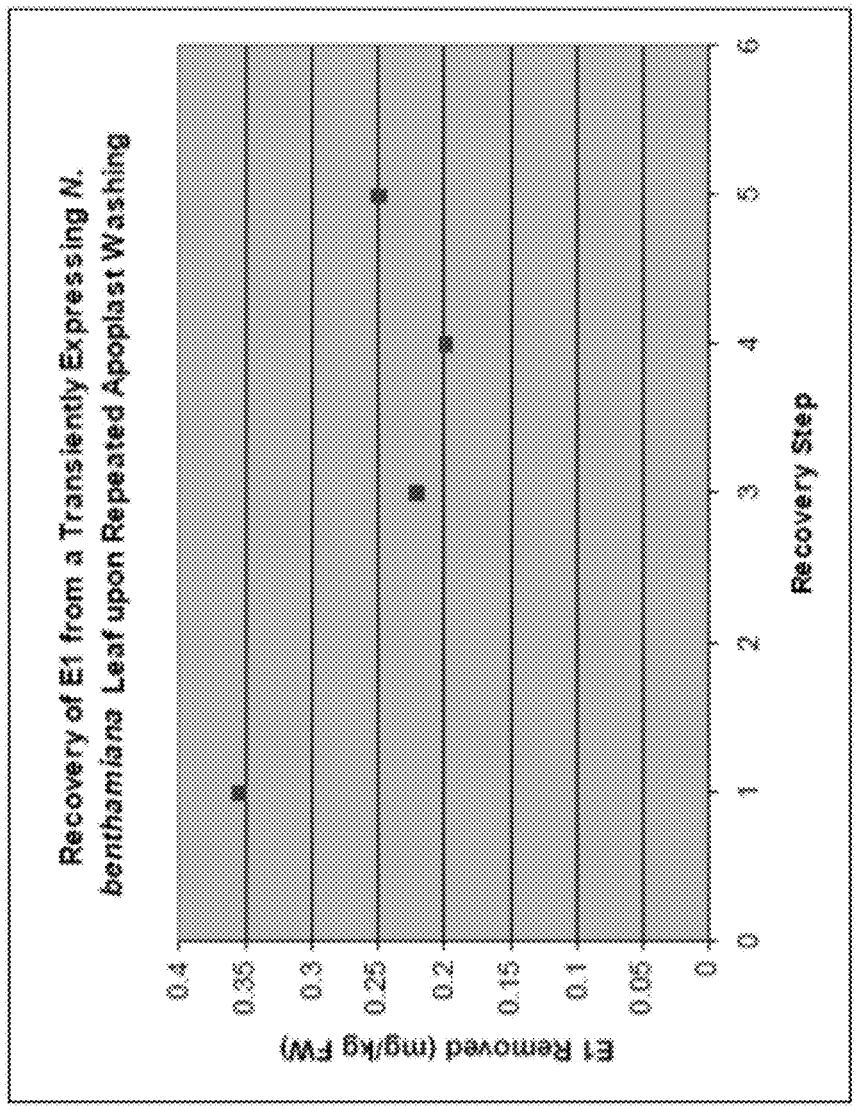
FIG. 36 depicts a *N. benthamiana* leaf transiently expressing the endoglucanase E1 after it had been subjected to five consecutive apoplast washes to remove secreted E1. Due to insufficient AWF volume, an activity assay for the second obtained AWF could not be performed.

Effectiveness of mechanical wounding treatment on sunflower leaves. The first step in *Agrobacterium* infection is the mechanical wounding process on the plant leaves and the wounded plant leaves release low molecular weight phenolic compounds that attract *Agrobacteria* and activate vir gene expression. Therefore, a natural wounding process might also enhance transient protein expression. In order to simulate a mechanical wounding process on the plant leaves, a plant leaf was pressed with a brush several times and then subjected to vacuum infiltration. FIG. 36 shows the direct comparison between with and without the wounding treatment. Compared with control leaves, the wounded plant leaves expressed more E1.

In conclusion, this example demonstrates that the production of heterologous protein in plant cells can be improved by adding plant hormones to *Agrobacterium* suspension solution before vacuum infiltration, shifting leaf incubation temperature during leaf incubation period, or mechanically wounding plant leaves.

Example 4

Apoplast Washing as a Means to Harvest Secreted Heterologous Proteins

This example assesses the efficiency of apoplast washing as an additional step to further improve methods for producing proteins, and especially secreted proteins, in plant cells.

Figure 34:
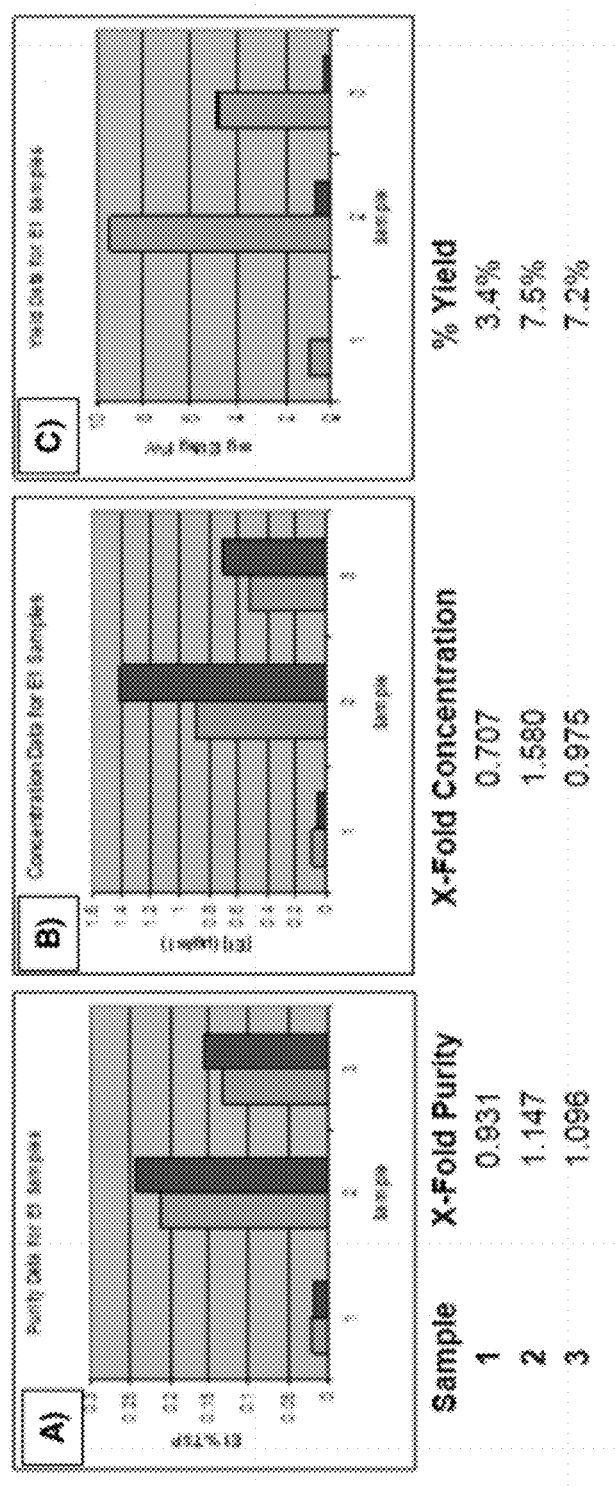
FIG. 34 depicts a comparison of values for the A) purity, B) concentration, and C) yields of E1 in homogenate extracts (HE; blue columns) and apoplast wash fluid (AWF; purple columns) obtained from three independent *N. benthamiana* leaves agroinfiltrated to transiently express E1. Values are for the first obtained AWF only. The table below the graphs represents the ratio of the values for the AWF divided by the value for the HE.

Recovery of proteins from the leaf interstitial fluid in agroinfiltrated leaves, quantification of E1 removed by apoplast washing. Recovery of recombinant enzymes from plant tissue is burdened by the high quantities of fiber and native plant proteases present in homogenate extracts (HE). Apoplast washing is a two-step process that removes the soluble components of the leaf apoplast (interstitial spaces between adjacent cells, outside of the cell membrane). First, an applied vacuum removes air bubbles from the interstitium of a leaf sample submerged in buffer and when that vacuum is released, buffer penetrates into the spaces in between cells. This buffer mixes with the aqueous contents of the leaf interstitium, which includes soluble secreted recombinant proteins such as the endoglucanase E1. Secondly, during a centrifugation step, this apoplast wash fluid (AWF) is removed along with the recombinant protein primarily through the stomata, leaving intact the plant leaf and the cells therein, theoretically enabling the leaf to continue to produce the protein of interest if left to incubate post-harvest. In one experiment, *N. benthamiana* leaves were infiltrated and transiently expressed the endoglucanase E1 for three days in a humidity chamber. The vacuum infiltration-centrifugation (VI-C) process was performed and the AWF was collected. In some variants of the experiment, the method was repeated four more times in an attempt to remove residual interstitially localized E1. The presence of E1 in the AWF and the washed homogenate was tested by activity assay and the presence of total soluble protein (TSP) was determined by Bradford assay to obtain values for the purity of E1 within each sample. The results for yield, purity, and concentration for three samples' HE and AWF are shown in FIG. 34. Leaf to leaf variability in the overall expression levels due to inconsistent agroinfiltration efficiency seems to be the primary reason for the variability in the other values.

In FIG. 36, the best results for E1 recovery are compared to the recovery of another protein produced within the experimental series described herein, as well as the results for the recovery of three different proteins as reported by the Large Scale Biology Corp. in U.S. Pat. No. 7,034,128.

Figure 37:
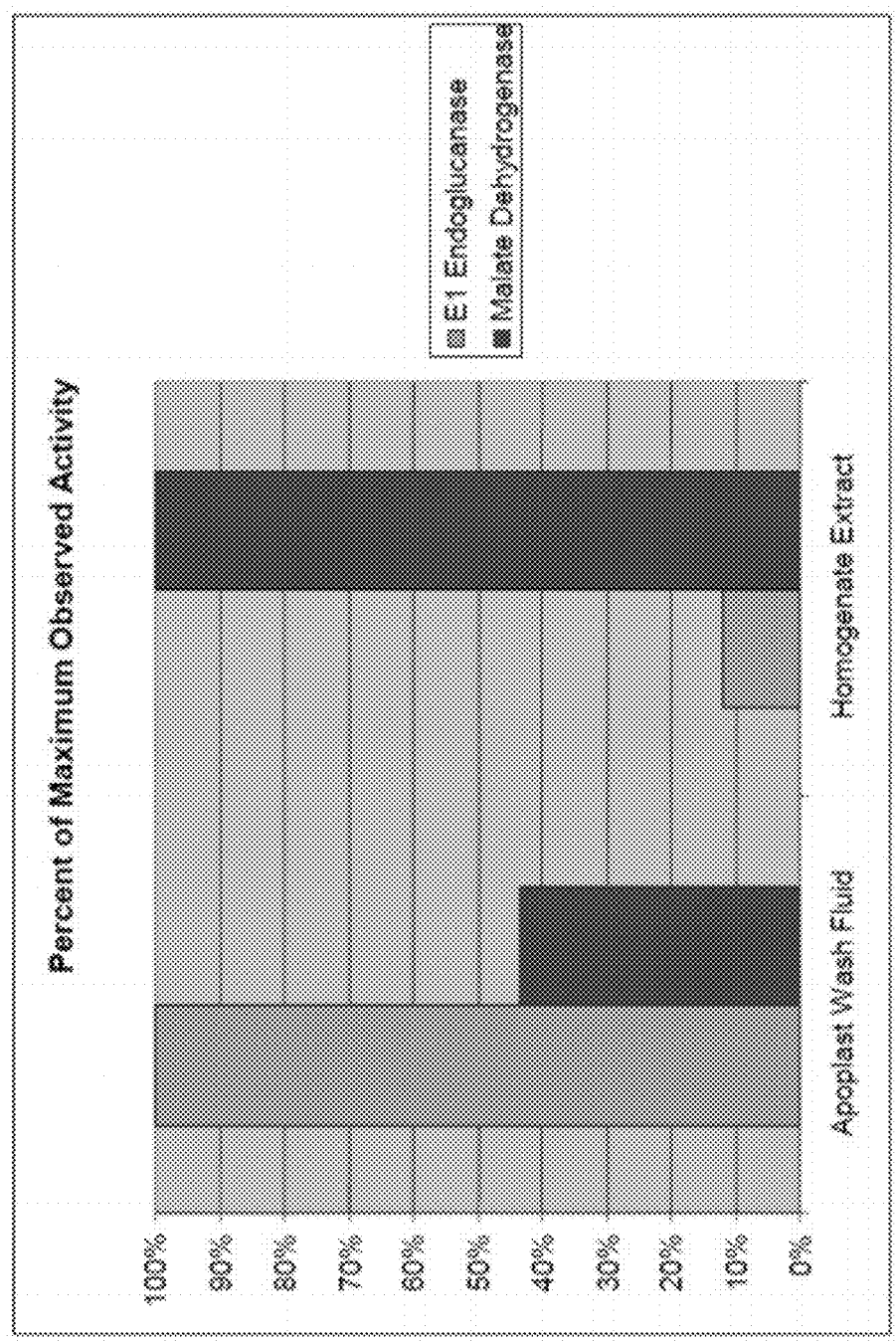
FIG. 37 depicts relative fractions of E1 and MDH activities in apoplast wash fluid (AWF) and homogenate extracts (HE) per mg of total soluble protein (TSP). The highest activity for each fraction was arbitrarily set at 100% for each comparison. E1 harvest buffer (0.1M NaCl, 0.05 M acetic acid, 0.1% Tween 80 or 0.01% Silwet L77) at pH 5.5 was used either as an infiltration buffer to recover the apoplast wash fluid, or for obtaining a homogenate extract. The activities of E1 and also of malate dehydrogenase (MDH), an intracellular marker were assayed in each. Each sample is the pooled AWF collected by spinning down four leaf discs excised from the same leaf.
Figure 38:
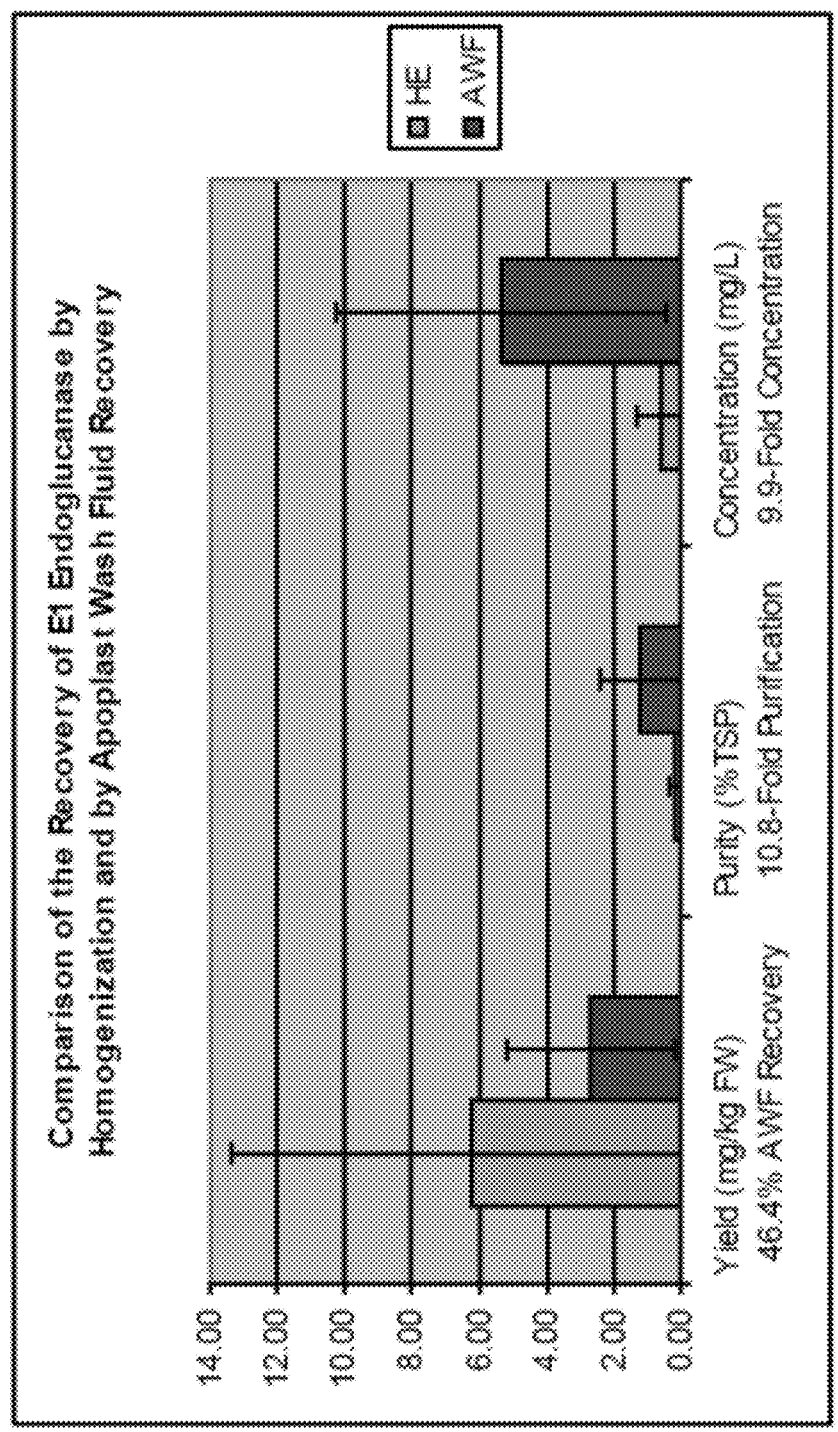
FIG. 38 depicts a comparison of the recovery of E1 endoglucanase by homogenization and by apoplast wash fluid recovery.

FIGS. 37 and 38, and Tables 2 and 3 show results of additional experiments determining relative enzyme activities in apoplast wash fluid and homogenate extract fractions. One experiment demonstrated that E1 endoglucanase may be selectively removed from interstitial spaces of leaf tissue (FIG. 37, Table 2). Specifically, it was shown that per mg total soluble protein the apoplast wash fluid had almost 10 times more E1 endoglucanase than the homogenate extract while possessing less than half the MDH activity of the homogenate extract (FIG. 37, Table 2). Another experiment demonstrated that the apoplast wash fluid can recover secreted recombinant proteins at enhanced purity and concentration levels (FIG. 37, Table 2). Specifically, significant improvements in purity and concentration of the E1 endoglucanase were achieved while losing only about half of the yield that is obtained by homogenate extraction. The concentration of the homogenate extraction was found to dependent strongly on the ratio of harvest buffer added per kg fresh weight (FW), which in these experiments were consistently held at 10 mL/g FW.

TABLE 2

Average Yields of E1 and MDH activity and total soluble protein (TSP) in six samples with high expression in E1

|  | AWF | HE |
|---|---|---|
| Avg MDH Activity (mmol NADH/min/kg FW) | 0.87 ± 0.28 | 54.22 ± 15.00 |
| Avg Soluble E1 (mg E1/kg FW) | 2.01 ± 2.72 | 6.46 ± 5.66 |
| Avg TSP (mg TSP/kg FW) | 197 ± 114 | 5110 ± 661 |
| Specific MDH (umol NADH/min/mg TSP) | 4.4 ± 2.9 | 10.6 ± 3.2 |
| Specific E1 (mg E1/mg TSP) | 0.010 ± 0.015 | 0.0013 ± 0.0011 |

TABLE 3

Yield, purity and concentration of E1 endoglucanase in apoplast wash fluid (AWE) and homogenate extracts (HE)

|  | Average | StDev | Maximum |
|---|---|---|---|
| Yield AWF (mg/kg FW) | 2.67 | 2.47 | 7.44 |
| Yield HE (mg/kg FW) | 6.26 | 7.17 | 21.95 |
| % Recovery | 46.4% | 12.1% | 63.3% |
| % E1 TSP AWF | 1.21% | 1.22% | 3.01% |
| % E1 TSP HE | 0.15% | 0.19% | 0.42% |
| X-Fold Purification | 10.82 | 4.44 | 17.25 |
| E1 AWF (mg/L) | 5.35 | 4.95 | 14.89 |
| E1 WHE (mg/L) | 0.58 | 0.67 | 2.05 |
| X-Fold Concentration | 9.92 | 2.58 | 13.56 |

This Table includes the standard deviations and the maximum values from seven samples.

In summary, this example demonstrates that secreted proteins can be harvested from plant tissue by apoplast washing and that the yields and purities of the harvested secreted proteins are dependent on the nature of the secreted protein, and possibly their propensity to adhere to solid plant materials, such as cell walls.

We claim:

1. A plant cell expressing a heterologous protein, the plant cell comprising a cucumber mosaic virus (CMV)-based viral amplicon, wherein the amplicon comprises multiple amplicon segments, capable of amplifying the transcription of a nucleic acid sequence encoding the heterologous protein, the amplicon comprising:
   a) a first amplicon segment comprising RNA 1 from CMV subgroup I,
   b) a second amplicon segment comprising RNA 2 from CMV subgroup I, and
   c) a third amplicon segment comprising RNA 3 from CMV subgroup II,
      wherein the nucleic acid sequence encoding the heterologous protein is present on the third amplicon segment.

2. The plant cell of claim 1, wherein the viral amplicon is encoded by a first and second plasmid, wherein the first plasmid comprises the first amplicon segment and the second amplicon segment, and the second plasmid encodes the third amplicon segment.

3. The plant cell of claim 1, wherein the viral amplicon is encoded by a first, second, and third plasmid, wherein the first plasmid comprises the first amplicon segment, the second plasmid comprises the second amplicon segment, and the third plasmid comprises the third amplicon segment.

4. The plant cell of claim 1, wherein the third amplicon segment comprises RNA 4.

5. The plant cell of claim 1, wherein the heterologous protein is an E1 β-1,4-endoglucanase from *Acidothermus cellulolyticus*.

6. The plant cell of claim 1, wherein the nucleic acid sequence encoding the heterologous protein further comprises a CaMV 35S promoter operably linked to the nucleic acid sequence encoding the heterologous protein.

7. The plant cell of claim 1, further comprising a cDNA encoding the gene silencing suppressor HcPro.

8. The plant cell of claim 1, wherein the RNA3 encodes a 33 amino acid C-terminal deletion mutant form of a CMV 3a movement protein.

9. The plant cell of claim 1, wherein the viral amplicon can replicate in planta and move systemically.

10. A method for producing a heterologous protein in a plant cell, said method comprising:
    a) agroinfiltrating the plant cell with *Agrobacterium*, the *Agrobacterium* comprising a cucumber mosaic virus (CMV)-based viral amplicon at a first temperature, wherein the amplicon comprises multiple amplicon segments, capable of amplifying the transcription of a nucleic acid sequence encoding the heterologous protein, the amplicon comprising:
       i) a first amplicon segment comprising RNA 1 from CMV subgroup I,
       ii) a second amplicon segment comprising RNA 2 from CMV subgroup I, and
       iii) a third amplicon segment comprising RNA 3 from CMV subgroup II, wherein the nucleic acid sequence encoding the heterologous protein is present on the third amplicon segment; and
    b) incubating the plant cell at a second temperature for a sufficient time to produce the heterologous protein in the plant cell.

11. The method of claim 10, wherein the heterologous protein is produced transiently in the plant cell.

12. The method of claim 10, wherein the heterologous protein is an enzyme capable of modifying, degrading, or decomposing plant cell walls.

13. The method of claim 10, wherein the heterologous protein is an E1 β-1,4-endoglucanase from *Acidothermus cellulolyticus*.

14. The method of claim 10, wherein four days are a sufficient time to produce the heterologous protein in the plant cell.

15. The method of claim 10, wherein the first temperature is 20° C. and the second temperature is 26° C. or 30° C.

* * * * *